(12) United States Patent
Thompson et al.

(10) Patent No.: US 10,470,911 B2
(45) Date of Patent: Nov. 12, 2019

(54) SLEEVE GASTRECTOMY CALIBRATION TUBE AND METHOD OF USING SAME

(71) Applicant: Standard Bariatrics, Inc., Cincinnati, OH (US)

(72) Inventors: Jonathan Thompson, Cincinnati, OH (US); John McKeown, Cincinnati, OH (US); Bennie Thompson, Cincinnati, OH (US)

(73) Assignee: Standard Bariatrics, Inc., Cincinnati, OH (US)

( * ) Notice: Subject to any disclaimer, the term of this patent is extended or adjusted under 35 U.S.C. 154(b) by 0 days.

(21) Appl. No.: 14/846,764

(22) Filed: Sep. 5, 2015

(65) Prior Publication Data

US 2016/0067074 A1    Mar. 10, 2016

Related U.S. Application Data

(60) Provisional application No. 62/046,598, filed on Sep. 5, 2014.

(51) Int. Cl.
*A61F 5/00* (2006.01)
*A61B 17/072* (2006.01)
*A61B 17/11* (2006.01)

(52) U.S. Cl.
CPC .......... *A61F 5/0083* (2013.01); *A61F 5/0076* (2013.01); *A61F 5/0086* (2013.01);
(Continued)

(58) Field of Classification Search
CPC .... A61F 5/0083; A61F 5/0076; A61F 5/0086; A61F 5/0089
See application file for complete search history.

(56) References Cited

U.S. PATENT DOCUMENTS

| 848,126 A | 3/1907 | Roosevelt |
| 1,413,896 A | 4/1922 | Brix |

(Continued)

FOREIGN PATENT DOCUMENTS

| EP | 0140552 A2 | 5/1985 |
| EP | 0666057 A2 | 8/1995 |

(Continued)

OTHER PUBLICATIONS

Geoffrey Parker, A New Stomach Clamp, 26 Postgrad Med. J. 550; 1 page.

(Continued)

*Primary Examiner* — Richard G Louis
(74) *Attorney, Agent, or Firm* — Ulmer & Berne LLP

(57) ABSTRACT

One or more medical devices may be provided that may be used, for example, in bariatric surgery including a vertical sleeve gastrectomy. The one or more medical devices may include a laparoscopic sleeve gastrectomy stapling guide in conjunction with a calibration tube in accordance with one or more examples. According to an example, the calibration tube may be a flared, multi-diameter calibration tube. The flared, multi-diameter calibration tube may have a first diameter along a portion of the tube and a second diameter that may larger than the first diameter along at least another portion of the tube. The calibration tube may be used in conjunction with the stapling guide to align stomach such that it may be stapled along the stapling guide (e.g., to perform the vertical sleeve gastrectomy).

8 Claims, 11 Drawing Sheets

(52) U.S. Cl.
CPC ...... *A61F 5/0089* (2013.01); *A61B 17/07207* (2013.01); *A61B 17/1114* (2013.01)

(56) References Cited

U.S. PATENT DOCUMENTS

| | | | |
|---|---|---|---|
| 2,659,371 A | 11/1953 | Schnee | |
| 2,686,520 A | 8/1954 | Jarvis et al. | |
| 3,490,675 A | 1/1970 | Green et al. | |
| 3,877,434 A | 4/1975 | Ferguson et al. | |
| 4,269,190 A | 5/1981 | Behney | |
| 4,442,964 A | 4/1984 | Becht | |
| 4,458,681 A | 7/1984 | Hopkins | |
| 4,520,817 A | 6/1985 | Green | |
| 4,527,724 A | 7/1985 | Chow et al. | |
| 4,558,699 A | 12/1985 | Bashour | |
| 4,605,004 A | 8/1986 | Di Giovanni et al. | |
| 4,608,981 A | 9/1986 | Rothfuss et al. | |
| 4,610,383 A | 9/1986 | Rothfuss et al. | |
| 4,784,137 A | 11/1988 | Kulik et al. | |
| 4,803,985 A | 2/1989 | Hill | |
| 4,819,853 A | 4/1989 | Green | |
| 4,848,637 A | 7/1989 | Pruitt | |
| 4,930,503 A | 6/1990 | Pruitt | |
| 4,951,861 A | 8/1990 | Schulze et al. | |
| 4,976,721 A | 12/1990 | Blasnik et al. | |
| 4,978,049 A | 12/1990 | Green | |
| 5,040,715 A | 8/1991 | Green et al. | |
| 5,205,459 A | 4/1993 | Brinkerhoff et al. | |
| 5,219,111 A | 6/1993 | Bilotti et al. | |
| 5,222,961 A | 6/1993 | Nakao et al. | |
| 5,307,976 A | 5/1994 | Olson | |
| 5,312,410 A | 5/1994 | Miller et al. | |
| 5,327,914 A | 7/1994 | Shlain | |
| 5,333,772 A | 8/1994 | Rothfuss et al. | |
| 5,345,949 A * | 9/1994 | Shlain | A61B 17/0682 128/898 |
| 5,395,034 A | 3/1995 | Allen et al. | |
| 5,415,334 A | 5/1995 | Williamson, IV et al. | |
| 5,431,323 A | 7/1995 | Smith et al. | |
| 5,443,475 A | 8/1995 | Auerbach et al. | |
| 5,452,836 A | 9/1995 | Huitema et al. | |
| 5,452,837 A | 9/1995 | Williamson, IV et al. | |
| 5,456,401 A | 10/1995 | Green et al. | |
| 5,465,895 A | 11/1995 | Knodel et al. | |
| 5,465,896 A | 11/1995 | Allen et al. | |
| 5,470,009 A | 11/1995 | Rodak | |
| 5,485,952 A | 1/1996 | Fontayne | |
| 5,487,500 A | 1/1996 | Knodel et al. | |
| 5,496,333 A | 3/1996 | Sackier et al. | |
| 5,507,426 A | 4/1996 | Young et al. | |
| 5,507,773 A | 4/1996 | Huitema et al. | |
| 5,531,744 A | 7/1996 | Nardella et al. | |
| 5,551,622 A | 9/1996 | Yoon | |
| 5,554,169 A | 9/1996 | Green et al. | |
| 5,560,530 A | 10/1996 | Bolanos et al. | |
| 5,562,702 A | 10/1996 | Huitema et al. | |
| 5,571,116 A | 11/1996 | Bolanos et al. | |
| 5,571,131 A | 11/1996 | Ek et al. | |
| 5,586,711 A | 12/1996 | Plyley et al. | |
| 5,597,107 A | 1/1997 | Knodel et al. | |
| 5,630,540 A | 5/1997 | Blewelt | |
| 5,632,432 A | 5/1997 | Schulze et al. | |
| 5,636,780 A | 6/1997 | Green et al. | |
| 5,662,667 A | 9/1997 | Knodel | |
| 5,697,542 A | 12/1997 | Knodel et al. | |
| 5,704,534 A | 1/1998 | Huitema et al. | |
| 5,732,871 A | 3/1998 | Clark et al. | |
| 5,762,256 A | 6/1998 | Mastri et al. | |
| 5,779,130 A | 7/1998 | Alesi et al. | |
| 5,779,132 A | 7/1998 | Knodel et al. | |
| 5,782,396 A | 7/1998 | Mastri et al. | |
| 5,797,538 A | 8/1998 | Heaton et al. | |
| 5,810,240 A | 9/1998 | Robertson | |
| 5,814,055 A | 9/1998 | Knodel et al. | |
| 5,820,009 A | 10/1998 | Melling et al. | |
| 5,865,361 A | 2/1999 | Milliman et al. | |
| 5,868,760 A | 2/1999 | McGuckin, Jr. | |
| 5,901,895 A | 5/1999 | Heaton et al. | |
| 5,954,259 A | 9/1999 | Viola et al. | |
| 5,964,394 A | 10/1999 | Robertson | |
| 5,988,479 A | 11/1999 | Palmer | |
| 6,032,849 A | 3/2000 | Mastri et al. | |
| 6,270,507 B1 | 8/2001 | Callicrate | |
| 6,325,810 B1 | 12/2001 | Hamilton et al. | |
| 6,505,768 B2 | 1/2003 | Whitman | |
| RE38,708 E | 3/2005 | Bolanos et al. | |
| 6,978,921 B2 | 12/2005 | Shelton, IV et al. | |
| 6,986,451 B1 | 1/2006 | Mastri et al. | |
| 6,988,649 B2 | 1/2006 | Shelton, IV et al. | |
| 7,025,791 B2 | 4/2006 | Levine et al. | |
| 7,032,799 B2 | 4/2006 | Viola et al. | |
| 7,037,344 B2 | 5/2006 | Kagan et al. | |
| 7,044,353 B2 | 5/2006 | Mastri et al. | |
| 7,070,083 B2 | 7/2006 | Jankowski | |
| 7,128,253 B2 | 10/2006 | Mastri et al. | |
| 7,134,587 B2 | 11/2006 | Schwemberger et al. | |
| 7,207,472 B2 | 4/2007 | Wukusick et al. | |
| 7,225,964 B2 | 6/2007 | Mastri et al. | |
| 7,229,428 B2 | 6/2007 | Gannoe et al. | |
| 7,235,089 B1 | 6/2007 | McGuckin, Jr. | |
| 7,258,262 B2 | 8/2007 | Mastri et al. | |
| 7,288,100 B2 | 8/2007 | Molina Trigueros | |
| 7,278,562 B2 | 10/2007 | Mastri et al. | |
| 7,278,563 B1 | 10/2007 | Green | |
| 7,308,998 B2 | 12/2007 | Mastri et al. | |
| RE40,237 E | 4/2008 | Bilotti et al. | |
| 7,401,721 B2 | 7/2008 | Holsten et al. | |
| 7,404,508 B2 | 7/2008 | Smith et al. | |
| 7,407,075 B2 | 8/2008 | Holsten et al. | |
| 7,407,076 B2 | 8/2008 | Racenet et al. | |
| 7,422,138 B2 | 9/2008 | Bilotti et al. | |
| 7,434,716 B2 | 10/2008 | Viola | |
| 7,434,717 B2 | 10/2008 | Shelton, IV et al. | |
| 7,455,676 B2 | 11/2008 | Holsten et al. | |
| 7,481,349 B2 | 1/2009 | Holsten et al. | |
| 7,500,979 B2 | 3/2009 | Hueil et al. | |
| 7,510,107 B2 | 3/2009 | Timm et al. | |
| 7,549,564 B2 | 6/2009 | Boudreaux | |
| 7,549,654 B2 | 6/2009 | Boudreaux | |
| 7,565,993 B2 | 7/2009 | Milliman et al. | |
| 7,588,177 B2 | 9/2009 | Racenet | |
| 7,617,961 B2 | 11/2009 | Viola | |
| 7,641,091 B2 | 1/2010 | Olson et al. | |
| 7,645,285 B2 | 1/2010 | Cosgrove et al. | |
| 7,658,312 B2 | 2/2010 | Vidal et al. | |
| 7,669,746 B2 | 3/2010 | Shelton, IV | |
| 7,673,781 B2 | 3/2010 | Swayze et al. | |
| 7,690,547 B2 | 4/2010 | Racenet et al. | |
| 7,708,684 B2 | 5/2010 | Demarais et al. | |
| 7,717,312 B2 | 5/2010 | Beetel | |
| 7,726,537 B2 | 6/2010 | Olson et al. | |
| 7,726,539 B2 | 6/2010 | Holsten et al. | |
| 7,731,072 B2 | 6/2010 | Timm et al. | |
| 7,770,774 B2 | 8/2010 | Mastri et al. | |
| D624,182 S | 9/2010 | Thouement | |
| 7,793,812 B2 | 9/2010 | Moore et al. | |
| 7,815,092 B2 | 10/2010 | Whitman et al. | |
| 7,819,896 B2 | 10/2010 | Racenet | |
| 7,828,188 B2 | 11/2010 | Jankowski | |
| 7,837,079 B2 | 11/2010 | Holsten et al. | |
| 7,857,184 B2 | 12/2010 | Viola | |
| 7,866,525 B2 | 1/2011 | Scirica | |
| 7,871,416 B2 | 1/2011 | Phillips | |
| 7,891,531 B1 | 2/2011 | Ward | |
| 7,891,533 B2 | 2/2011 | Green et al. | |
| 7,913,893 B2 | 3/2011 | Mastri et al. | |
| 7,918,869 B2 | 4/2011 | Saadat et al. | |
| 7,934,630 B2 | 5/2011 | Shelton, IV et al. | |
| 7,959,050 B2 | 6/2011 | Smith et al. | |
| 7,992,757 B2 | 8/2011 | Wheeler et al. | |
| 8,016,176 B2 | 9/2011 | Kasvikis et al. | |
| 8,020,741 B2 | 9/2011 | Cole et al. | |
| 8,028,884 B2 | 10/2011 | Sniffin et al. | |
| 8,033,442 B2 | 10/2011 | Racenet et al. | |

(56) References Cited

U.S. PATENT DOCUMENTS

| | | |
|---|---|---|
| 8,034,077 B2 | 10/2011 | Smith et al. |
| 8,056,788 B2 | 11/2011 | Mastri et al. |
| 8,061,577 B2 | 11/2011 | Racenet et al. |
| 8,062,236 B2 | 11/2011 | Soltz |
| 8,066,168 B2 | 11/2011 | Vidal et al. |
| 8,070,034 B1 | 12/2011 | Knodel |
| 8,087,563 B2 | 1/2012 | Milliman et al. |
| 8,096,459 B2 | 1/2012 | Ortiz et al. |
| 8,132,704 B2 | 3/2012 | Whitman et al. |
| 8,141,762 B2 | 3/2012 | Bedi et al. |
| 8,167,186 B2 | 5/2012 | Racenet et al. |
| 8,196,795 B2 | 6/2012 | Moore et al. |
| 8,205,780 B2 | 6/2012 | Sorrentino et al. |
| 8,226,602 B2 | 7/2012 | Quijana et al. |
| 8,245,898 B2 | 8/2012 | Smith et al. |
| 8,252,009 B2 | 8/2012 | Weller et al. |
| 8,256,655 B2 | 9/2012 | Sniffin et al. |
| 8,276,801 B2 | 10/2012 | Zemlok et al. |
| 8,308,725 B2 | 11/2012 | Bell et al. |
| 8,322,455 B2 | 12/2012 | Shelton, IV et al. |
| 8,328,061 B2 | 12/2012 | Kasvikis |
| 8,328,064 B2 | 12/2012 | Racenet et al. |
| 8,348,129 B2 | 1/2013 | Bedi et al. |
| 8,348,130 B2 | 1/2013 | Shah et al. |
| 8,365,973 B1 | 2/2013 | White et al. |
| 8,382,775 B1 | 2/2013 | Bender et al. |
| 8,403,956 B1 | 3/2013 | Thompson et al. |
| 8,408,442 B2 | 4/2013 | Racenet et al. |
| 8,424,739 B2 | 4/2013 | Racenet et al. |
| 8,439,244 B2 | 5/2013 | Holcolmb et al. |
| 8,439,246 B1 | 5/2013 | Knodel |
| 8,449,560 B2 | 5/2013 | Roth et al. |
| 8,453,912 B2 | 6/2013 | Mastri et al. |
| 8,453,914 B2 | 6/2013 | Laurent et al. |
| 8,464,923 B2 | 6/2013 | Shelton, IV |
| 8,465,507 B2 | 6/2013 | Cosgrove et al. |
| 8,496,155 B2 | 7/2013 | Knodel |
| 8,496,156 B2 | 7/2013 | Sniftin et al. |
| 8,529,585 B2 | 9/2013 | Jacobs et al. |
| 8,540,128 B2 | 9/2013 | Shelton, IV et al. |
| 8,540,130 B2 | 9/2013 | Moore et al. |
| 8,544,712 B2 | 10/2013 | Jankowski |
| 8,561,872 B2 | 10/2013 | Wheeler et al. |
| 8,579,176 B2 | 11/2013 | Smith et al. |
| 8,579,178 B2 | 11/2013 | Holsten et al. |
| 8,596,513 B2 | 12/2013 | Olson et al. |
| 8,608,043 B2 | 12/2013 | Scirica |
| 8,613,384 B2 | 12/2013 | Pastorelli et al. |
| 8,617,185 B2 | 12/2013 | Bonutti et al. |
| 8,628,544 B2 | 1/2014 | Farascioni |
| 8,628,547 B2 | 1/2014 | Weller et al. |
| 8,647,350 B2 | 2/2014 | Mohan et al. |
| 8,663,245 B2 | 3/2014 | Francischelli et al. |
| 8,672,830 B2 | 3/2014 | Dlugos, Jr. et al. |
| 8,701,958 B2 | 4/2014 | Shelton, IV et al. |
| 8,714,429 B2 | 5/2014 | Demmy |
| 8,733,613 B2 | 5/2014 | Huitema et al. |
| 8,740,035 B2 | 6/2014 | Mastri et al. |
| 8,758,392 B2 | 6/2014 | Crainich |
| 8,801,732 B2 | 8/2014 | Harris et al. |
| 8,852,218 B2 | 10/2014 | Hughett, Sr. et al. |
| 8,864,009 B2 | 10/2014 | Shelton, IV et al. |
| 8,899,465 B2 | 12/2014 | Shelton, IV et al. |
| 8,945,163 B2 | 2/2015 | Voegele et al. |
| 8,991,677 B2 | 3/2015 | Moore et al. |
| 8,998,058 B2 | 4/2015 | Moore et al. |
| 9,016,541 B2 | 4/2015 | Viola et al. |
| 9,084,600 B1 | 7/2015 | Knodel et al. |
| 9,084,601 B2 | 7/2015 | Moore et al. |
| 9,095,339 B2 | 8/2015 | Moore et al. |
| 9,113,862 B2 | 8/2015 | Morgan et al. |
| 9,113,868 B2 | 8/2015 | Felder et al. |
| 9,138,226 B2 | 9/2015 | Racenet et al. |
| 9,155,528 B2 | 10/2015 | Bender et al. |
| 9,168,039 B1 | 10/2015 | Knodel |
| 9,180,035 B2 | 11/2015 | Stack et al. |
| 9,314,362 B2 | 4/2016 | Bender et al. |
| 9,339,442 B2 | 5/2016 | Tai et al. |
| 9,345,478 B2 | 5/2016 | Knodel |
| 9,364,225 B2 | 6/2016 | Sniffin et al. |
| 9,370,362 B2 | 6/2016 | Petty et al. |
| 9,398,917 B2 | 7/2016 | Whitfield et al. |
| 9,433,411 B2 | 9/2016 | Racenet et al. |
| 9,439,633 B2 | 9/2016 | O'Dea |
| 9,498,219 B2 | 11/2016 | Moore et al. |
| 9,603,598 B2 | 3/2017 | Shelton, IV et al. |
| 9,615,952 B2 | 4/2017 | Scott et al. |
| 9,636,114 B2 | 5/2017 | Cole et al. |
| 9,675,355 B2 | 6/2017 | Shelton, IV et al. |
| 9,687,233 B2 | 6/2017 | Fernandez et al. |
| 9,700,321 B2 | 7/2017 | Shelton, IV et al. |
| 9,724,091 B2 | 8/2017 | Shelton, IV et al. |
| 9,724,096 B2 | 8/2017 | Thompson et al. |
| 9,730,692 B2 | 8/2017 | Shelton, IV et al. |
| 9,775,613 B2 | 10/2017 | Shelton, IV et al. |
| 9,801,627 B2 | 10/2017 | Harris et al. |
| 9,801,628 B2 | 10/2017 | Harris et al. |
| 9,808,246 B2 | 11/2017 | Shelton, IV et al. |
| 9,820,742 B2 | 11/2017 | Covach et al. |
| 9,827,002 B2 | 11/2017 | Hausen et al. |
| 9,936,953 B2 | 4/2018 | Thompson et al. |
| 10,231,734 B2 | 3/2019 | Thompson et al. |
| 10,278,699 B2 | 5/2019 | Thompson et al. |
| 10,278,707 B2 | 5/2019 | Thompson et al. |
| 10,285,837 B1 | 5/2019 | Thompson et al. |
| 2003/0125734 A1 | 7/2003 | Mollenauer |
| 2004/0006351 A1 | 1/2004 | Gannoe et al. |
| 2004/0068267 A1 | 4/2004 | Harvie et al. |
| 2004/0181239 A1 | 9/2004 | Dorn et al. |
| 2005/0006432 A1 | 1/2005 | Racenet et al. |
| 2005/0080444 A1* | 4/2005 | Kraemer ............ A61B 17/122 606/192 |
| 2005/0139633 A1 | 6/2005 | Wukusick et al. |
| 2005/0203547 A1 | 9/2005 | Weller et al. |
| 2006/0016853 A1 | 1/2006 | Racenet |
| 2006/0085030 A1 | 4/2006 | Bettuchi et al. |
| 2006/0151568 A1 | 7/2006 | Weller et al. |
| 2006/0229665 A1 | 10/2006 | Wales et al. |
| 2006/0241692 A1 | 10/2006 | McGuckin et al. |
| 2007/0023477 A1 | 2/2007 | Whitman et al. |
| 2007/0027469 A1 | 2/2007 | Smith et al. |
| 2007/0029364 A1 | 2/2007 | Kruszynski et al. |
| 2007/0034666 A1 | 2/2007 | Holsten et al. |
| 2007/0039997 A1 | 2/2007 | Mather et al. |
| 2007/0075114 A1 | 4/2007 | Shelton, IV et al. |
| 2007/0083233 A1 | 4/2007 | Ortiz et al. |
| 2007/0131732 A1 | 6/2007 | Holsten et al. |
| 2007/0179528 A1 | 8/2007 | Soltz et al. |
| 2007/0194079 A1* | 8/2007 | Hueil ............... A61B 17/072 227/176.1 |
| 2007/0194081 A1 | 8/2007 | Hueil et al. |
| 2007/0213743 A1 | 9/2007 | McGuckin, Jr. |
| 2007/0246505 A1 | 10/2007 | Pace-Floridia et al. |
| 2008/0015631 A1 | 1/2008 | Lee et al. |
| 2008/0023522 A1 | 1/2008 | Olson et al. |
| 2008/0033457 A1 | 2/2008 | Francischelli et al. |
| 2008/0078800 A1 | 4/2008 | Hess et al. |
| 2008/0087707 A1 | 4/2008 | Jankowski |
| 2008/0164297 A1 | 7/2008 | Holsten et al. |
| 2008/0169329 A1 | 7/2008 | Shelton et al. |
| 2008/0169332 A1* | 7/2008 | Shelton ............ A61B 17/07207 227/180.1 |
| 2008/0190990 A1 | 8/2008 | Holsten et al. |
| 2008/0203134 A1 | 8/2008 | Shah et al. |
| 2008/0249404 A1 | 10/2008 | Mikkaichi et al. |
| 2008/0275480 A1 | 11/2008 | Jacobs et al. |
| 2009/0012556 A1 | 1/2009 | Boudreaux et al. |
| 2009/0209946 A1 | 8/2009 | Swayze et al. |
| 2009/0209986 A1 | 8/2009 | Stewart et al. |
| 2009/0308907 A1 | 12/2009 | Nalagatla et al. |
| 2010/0010512 A1 | 1/2010 | Taylor et al. |
| 2010/0072258 A1 | 3/2010 | Farascioni et al. |
| 2010/0114124 A1 | 5/2010 | Kelleher et al. |
| 2010/0121356 A1 | 5/2010 | Hartmann et al. |

(56) References Cited

U.S. PATENT DOCUMENTS

| | | |
|---|---|---|
| 2010/0145324 A1 | 6/2010 | Nihalani |
| 2010/0213240 A1 | 8/2010 | Kostrzewski |
| 2010/0256634 A1 | 10/2010 | Voegele et al. |
| 2010/0282820 A1 | 11/2010 | Kasvikis |
| 2010/0331866 A1 | 12/2010 | Surti et al. |
| 2011/0017800 A1 | 1/2011 | Viola |
| 2011/0071555 A1 | 3/2011 | McBrayer et al. |
| 2011/0084113 A1 | 4/2011 | Bedi et al. |
| 2011/0087279 A1 | 4/2011 | Shah et al. |
| 2011/0152895 A1 | 6/2011 | Nyuli et al. |
| 2011/0160752 A1 | 6/2011 | Aguirre |
| 2011/0178454 A1 | 6/2011 | Gagner et al. |
| 2011/0190791 A1 | 8/2011 | Jacobs et al. |
| 2011/0208211 A1 | 8/2011 | Whitfield et al. |
| 2011/0278343 A1 | 11/2011 | Knodel et al. |
| 2012/0059400 A1 | 3/2012 | Williamson, IV et al. |
| 2012/0123463 A1 | 5/2012 | Jacobs |
| 2012/0175398 A1 | 7/2012 | Sandborn et al. |
| 2012/0203247 A1 | 8/2012 | Shelton, IV et al. |
| 2012/0277525 A1 | 11/2012 | O'Dea |
| 2012/0286022 A1 | 11/2012 | Olson et al. |
| 2013/0062394 A1 | 3/2013 | Smith et al. |
| 2013/0075447 A1 | 3/2013 | Weisenburgh, II et al. |
| 2013/0075450 A1 | 3/2013 | Schmid et al. |
| 2013/0146638 A1 | 6/2013 | Mandakolathur Vasudevan et al. |
| 2013/0146642 A1 | 6/2013 | Shelton, IV et al. |
| 2013/0153625 A1 | 6/2013 | Felder et al. |
| 2013/0153642 A1 | 6/2013 | Felder et al. |
| 2013/0161374 A1 | 6/2013 | Swayze et al. |
| 2013/0165774 A1* | 6/2013 | Nocca ............... A61F 5/0083 600/431 |
| 2013/0172929 A1 | 7/2013 | Hess et al. |
| 2013/0245652 A1 | 9/2013 | Cosgrove et al. |
| 2013/0256375 A1 | 10/2013 | Shelton, IV et al. |
| 2013/0284791 A1 | 10/2013 | Olson et al. |
| 2013/0327809 A1 | 12/2013 | Shelton, IV et al. |
| 2013/0341374 A1 | 12/2013 | Shelton, IV et al. |
| 2014/0027493 A1 | 1/2014 | Jankowski |
| 2014/0046345 A1 | 2/2014 | Armenteros et al. |
| 2014/0074131 A1 | 3/2014 | Armenteros et al. |
| 2014/0082497 A1 | 3/2014 | Chalouhi et al. |
| 2014/0107698 A1 | 4/2014 | Inge |
| 2014/0114121 A1 | 4/2014 | Trivedi |
| 2014/0131418 A1 | 5/2014 | Kostrzewski |
| 2014/0131419 A1 | 5/2014 | Bettuchi |
| 2014/0184519 A1 | 7/2014 | Benchenaa et al. |
| 2014/0231489 A1 | 8/2014 | Balbierz et al. |
| 2014/0257353 A1 | 9/2014 | Whitman et al. |
| 2014/0276932 A1 | 9/2014 | Williams et al. |
| 2014/0291379 A1 | 10/2014 | Schellin et al. |
| 2015/0048141 A1 | 2/2015 | Felder et al. |
| 2015/0083780 A1 | 3/2015 | Shelton, IV et al. |
| 2015/0157318 A1 | 6/2015 | Beardsley et al. |
| 2015/0173755 A1 | 6/2015 | Baxter, III et al. |
| 2015/0209034 A1 | 7/2015 | Viola et al. |
| 2015/0265276 A1 | 9/2015 | Huitema et al. |
| 2015/0320423 A1 | 11/2015 | Aranyi |
| 2016/0058447 A1 | 3/2016 | Posada et al. |
| 2016/0067074 A1 | 3/2016 | Thompson et al. |
| 2016/0166256 A1 | 6/2016 | Baxter, III et al. |
| 2016/0183945 A1 | 6/2016 | Shelton, IV et al. |
| 2016/0199061 A1 | 7/2016 | Shelton, IV et al. |
| 2016/0199088 A1 | 7/2016 | Shelton, IV et al. |
| 2016/0235409 A1 | 8/2016 | Shelton, IV et al. |
| 2016/0242768 A1 | 8/2016 | Moore et al. |
| 2016/0242769 A1 | 8/2016 | Moore et al. |
| 2016/0242770 A1 | 8/2016 | Moore et al. |
| 2016/0242783 A1 | 8/2016 | Shelton, IV et al. |
| 2016/0262744 A1 | 9/2016 | Milo et al. |
| 2016/0262750 A1 | 9/2016 | Hausen et al. |
| 2016/0270792 A1 | 9/2016 | Sniffin et al. |
| 2016/0324527 A1 | 11/2016 | Thompson et al. |
| 2016/0367250 A1 | 12/2016 | Racenet et al. |
| 2017/0014125 A1 | 1/2017 | Shelton, IV et al. |
| 2017/0095251 A1 | 4/2017 | Thompson et al. |
| 2017/0172571 A1 | 6/2017 | Thompson et al. |
| 2017/0231633 A1 | 8/2017 | Marczyk et al. |
| 2017/0290588 A1 | 10/2017 | Thompson et al. |
| 2017/0303952 A1 | 10/2017 | Nativ et al. |
| 2017/0319210 A1 | 11/2017 | Moore et al. |
| 2017/0333041 A1 | 11/2017 | Moore et al. |
| 2019/0046189 A1 | 2/2019 | Dunki-Jacobs et al. |

FOREIGN PATENT DOCUMENTS

| | | |
|---|---|---|
| EP | 0399699 B1 | 11/1995 |
| EP | 0503662 B1 | 6/1997 |
| EP | 1090592 A1 | 4/2001 |
| EP | 1769766 A1 | 4/2007 |
| EP | 1806101 A1 | 7/2007 |
| EP | 1875868 A1 | 1/2008 |
| EP | 1875870 A1 | 1/2008 |
| EP | 2005896 A2 | 12/2008 |
| EP | 2005898 A2 | 12/2008 |
| EP | 1774916 B1 | 2/2009 |
| EP | 2090247 A1 | 8/2009 |
| EP | 2111803 A2 | 10/2009 |
| EP | 2319424 A1 | 5/2011 |
| EP | 2019633 B1 | 8/2012 |
| WO | 01/54594 A1 | 8/2001 |
| WO | 03/094747 A1 | 11/2003 |
| WO | 2007/009099 A2 | 1/2007 |
| WO | 2007/019268 A2 | 2/2007 |
| WO | 2007/102152 A2 | 9/2007 |
| WO | 2008/042022 A1 | 4/2008 |
| WO | 2010/011661 A1 | 1/2010 |
| WO | 2011/044032 A3 | 4/2011 |
| WO | 2012/141679 A1 | 10/2012 |
| WO | WO 2012141679 A1 * | 10/2012 ......... A61B 17/0644 |
| WO | 2013/151888 A1 | 10/2013 |
| WO | 2014/085099 A1 | 6/2014 |

OTHER PUBLICATIONS

Parikh, M.D. et al., Surgical Strategies That May Decrease Leak After Laparoscopic Sleeve Gastrectomy, 257 Annals of Surgery 231, Feb. 2013; 7 pages.

Aladar de Petz, M.D., Aseptic Technic of Stomach Resections, 86 Annals of Surgery 388, Sep. 1927; 5 pages.

John D. Harrah, M.D., A Lung Clamp for Use with Mechanical Staplers, 28 The Annals of Thoracic Surgery 489, Nov. 1979; 2 pages.

Bram D. Zuckerman, M.D., Food and Drug Administration, Letter to AtriCure, Inc. Addressing Indication for Use of AtriClip LAA Exclusion System w/Pre-loaded Gillnov-Cosgrove Clip, Jun. 10, 2010; 3 pages.

510(k) Summary for AtriClip LAA Exclusion System with preloaded Gillnov-Cosgrove Clip, published Jun. 10, 2010; 6 pages.

CMS Description of Open Left Atrial Appendage Occlusion with "U" Fastener Implant, Received Aug. 7, 2011; 1 page.

510(k) Summary for TigerPaw(R) System, published Oct. 29, 2010; 6 pages.

Pfiedler Enterprises, Science of Stapling: Urban Legend and Fact, Published Jun. 4, 2012; 38 pages.

Written Opinion of the Int'l Searching Authority and International Search Report for PCT/US2015/048740 dated Feb. 17, 2016; 12 pages.

Written Opinion of the Int'l Searching Authority and International Search Report for PCT/US2015/022990 dated Sep. 30, 2015; 10 pages.

Written Opinion of the Int'l Searching Authority and International Search Report for PCT/US2015/022904 dated Jun. 25, 2015; 6 pages.

Search Report and Written Opinion of the International Searching Authority for International Patent App. No. PCT/US2014/070869 dated Apr. 24, 2015; 11 pages.

Supplementary European Search Report of the European Patent Office, Issued in European Application No. 15772561.5-1664; dated Mar. 15, 2017; 8 pages.

(56) References Cited

OTHER PUBLICATIONS

International Preliminary Report on Patentability and Written Opinion of the International Searching Authority in Application No. PCT/US2015/048740 dated Mar. 7, 2017; 8 pages.
Supplementary European Search Report of the European Patent Office, Issued in European Application No. 14872137.6-1664/ 3082620; dated Mar. 28, 2017; 15 pages.
Australian Examination Report in Application No. 2016208416; dated May 18, 2017; 4 pages.
European Search Report of the European Patent Office, Issued in European Application No. 15774247.9-1654; dated Dec. 23, 2016; 11 pages.
Supplementary Partial European Search Report of the European Patent Office, Issued in European Application No. 14872137; dated Dec. 12, 2016; 5 pages.
M Jacobs et al., Laparoscopic sleeve gastrectomy: a retrospective review of 1- and 2-year results, Surg Endosc. Apr. 2010;24(4):781-5. doi: 10.1007/s00464-009-0619-8. Epub Aug. 19, 2009; abstract only; 2 pages.
JP Regan et al., Early experience with two-stage laparoscopic Roux-en-Y gastric bypass as an alternative in the super-super obese patient, Obes Surg. Dec. 2003;13(6):861-4; abstract only; 2 pages.
Australian Examination Report in Application No. 2015241267; dated Feb. 25, 2019; 6 pages.
Australian Examination Report in Application No. 2018203527; dated Oct. 22, 2018; 5 pages.
International Search Report and Written Opinion of the International Searching Authority for International Patent App. No. PCT/US2018/046743 dated Dec. 4, 2018; 20 pages.
Australian Examination Report in Application No. 2015241193; dated Dec. 11, 2018; 5 pages.
Examination Report of the European Patent Office, Issued in European Application No. 15772561.5-1122, dated Oct. 29, 2018; 7 pages.
Search Report of the State Intellectual Property Office of the People's Republic of China, Issued in Chinese Application No. 201480075706.2; dated Nov. 28, 2018; 3 pages.
Felicien M. Steichen and Mark M. Ravitch, Stapling in Surgery, Figure 1-11C, Year Book Medical Publishers, Inc. 1984; 3 pages.

\* cited by examiner

F1
$$C_1 + 2L_1 = C_2$$
FIG. 13A
F2
$$D_1 + \frac{2L_1}{\pi} = D_2$$
FIG. 13B
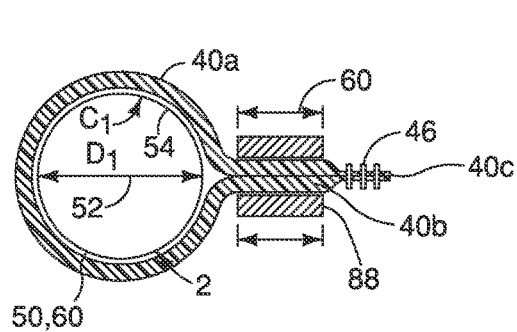
FIG. 14A
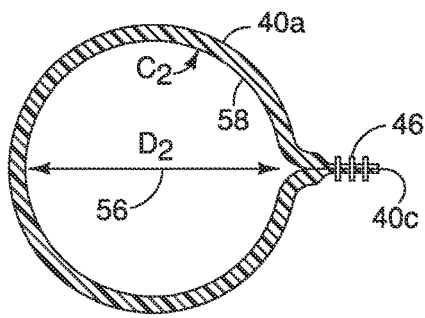
FIG. 14B

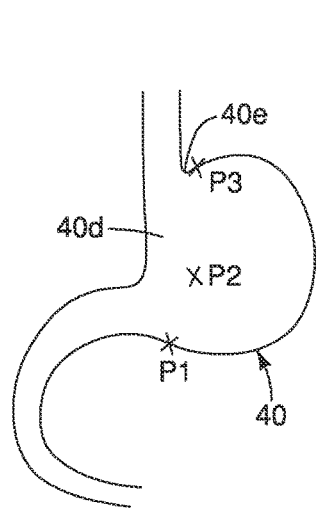
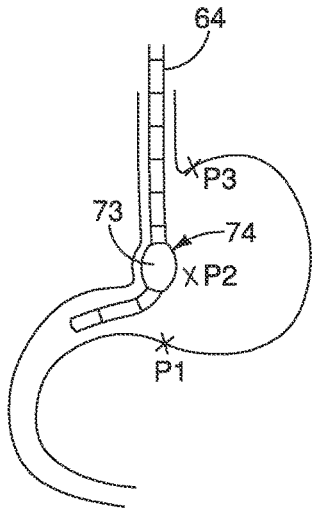
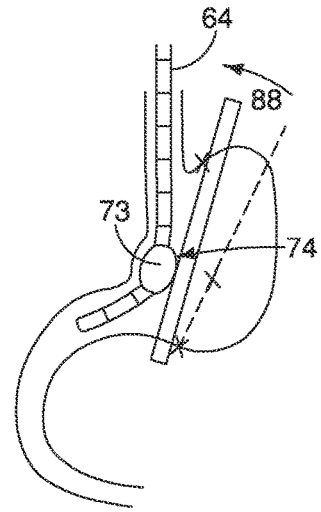
FIG. 19      FIG. 20      FIG. 21
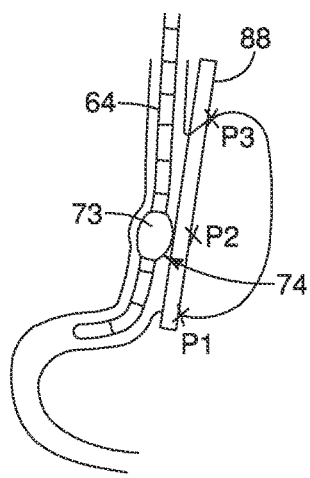
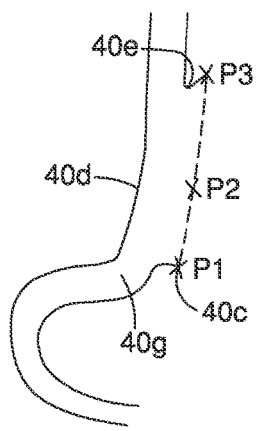
FIG. 22      FIG. 23

| Tube size (Fr) | 0 | 5 | 6 | 7 | 8 | 9 | 10 |
|---|---|---|---|---|---|---|---|
| 10 | 10.00 | 19.55 | 21.46 | 23.37 | 25.28 | 27.19 | 29.10 |
| 12 | 12 | 21.55 | 23.46 | 25.37 | 27.28 | 29.19 | 31.10 |
| 14 | 14 | 23.55 | 25.46 | 27.37 | 29.28 | 31.19 | 33.10 |
| 16 | 16 | 25.55 | 27.46 | 29.37 | 31.28 | 33.19 | 35.10 |
| 18 | 18 | 27.55 | 29.46 | 31.37 | 33.28 | 35.19 | 37.10 |
| 20 | 20 | 29.55 | 31.46 | 33.37 | 35.28 | 37.19 | 39.10 |
| 22 | 22 | 31.55 | 33.46 | 35.37 | 37.28 | 39.19 | 41.10 |
| 24 | 24 | 33.55 | 35.46 | 37.37 | 39.28 | 41.19 | 43.10 |
| 26 | 26 | 35.55 | 37.46 | 39.37 | 41.28 | 43.19 | 45.10 |
| 28 | 28 | 37.55 | 39.46 | 41.37 | 43.28 | 45.19 | 47.10 |
| 30 | 30 | 39.55 | 41.46 | 43.37 | 45.28 | 47.19 | 49.10 |
| 32 | 32 | 41.55 | 43.46 | 45.37 | 47.28 | 49.19 | 51.10 |
| 34 | 34 | 43.55 | 45.46 | 47.37 | 49.28 | 51.19 | 53.10 |
| 36 | 36 | 45.55 | 47.46 | 49.37 | 51.28 | 53.19 | 55.10 |
| 38 | 38 | 47.55 | 49.46 | 51.37 | 53.28 | 55.19 | 57.10 |
| 40 | 40 | 49.55 | 51.46 | 53.37 | 55.28 | 57.19 | 59.10 |
| 42 | 42 | 51.55 | 53.46 | 55.37 | 57.28 | 59.19 | 61.10 |
| 44 | 44 | 53.55 | 55.46 | 57.37 | 59.28 | 61.19 | 63.10 |
| 46 | 46 | 55.55 | 57.46 | 59.37 | 61.28 | 63.19 | 65.10 |
| 48 | 48 | 57.55 | 59.46 | 61.37 | 63.28 | 65.19 | 67.10 |
| 50 | 50 | 59.55 | 61.46 | 63.37 | 65.28 | 67.19 | 69.10 |
| 52 | 52 | 61.55 | 63.46 | 65.37 | 67.28 | 69.19 | 71.10 |
| 54 | 54 | 63.55 | 65.46 | 67.37 | 69.28 | 71.19 | 73.10 |
| 56 | 56 | 65.55 | 67.46 | 69.37 | 71.28 | 73.19 | 75.10 |
| 58 | 58 | 67.55 | 69.46 | 71.37 | 73.28 | 75.19 | 77.10 |
| 60 | 60 | 69.55 | 71.46 | 73.37 | 75.28 | 77.19 | 79.10 |

FIG. 33

SLEEVE GASTRECTOMY CALIBRATION TUBE AND METHOD OF USING SAME

CROSS-REFERENCE TO RELATED APPLICATIONS

This application claims the benefit of U.S. Provisional Application No. 62/046,598, filed Sep. 5, 2014, the disclosures of which are incorporated herein by references in their entirety.

TECHNICAL FIELD

The examples herein may be directed to a sleeve gastrectomy, and more particularly to a calibration tube inserted into the stomach and used in conjunction with a sleeve gastrectomy stapling guide or a sleeve gastrectomy stapler such as a full length sleeve gastrectomy stapler. The example devices herein may provide a minimum safe distance from the incisura angularis and other stomach landmarks during the creation of a vertical sleeve gastrectomy.

BACKGROUND

Obesity is a disease that affects a significant portion of the world's population and leads to multiple chronic medical conditions and premature death from cardiovascular events and cancer. In particular, the United States has a current, and worsening obesity epidemic. The U.S. Centers for Disease Control and Prevention (CDC) reports that over 33% of the U.S. population is obese, with a Body Mass Index (BMI) of over 30, and another 35-40% of the US population is overweight, with a BMI of 25-30. The CDC reports that the percent of the US population being either overweight or obese by 2018 will be 75%. The CDC also reports that obesity directly costs the U.S. economy $147 billion currently, and projects that the costs will approach $315 billion by 2020.

Further, obesity has environmental, genetic and behavioral origins but is intractable to most medical and behavioral interventions. To help reduce obesity and/or facilitate weight loss, bariatric surgery may be an option for some patients that may be overweight. Typically, bariatric surgery may be an effective long-term treatment option for patients with a BMI greater than 35. Despite the 20 million patients who are eligible for weight loss surgery in the U.S., the number of procedures per year has plateaued at about 200 thousand, eliminating any public health effect of surgery.

In recent years, a popular form of bariatric surgery may include a laparoscopic vertical sleeve gastrectomy (e.g., which may remove approximately 80% of the stomach). Laparoscopic vertical sleeve gastrectomy may be a procedure that may be safer and more effective for patients eligible for weight loss surgery. In fact, it has been accepted as the surgery that should be offered to most morbidly obese patients over, for example, laparoscopic adjustable gastric banding and laparoscopic Roux-en-Y gastric bypass. As such, the surgery has been adopted by bariatric surgeons and is now the most commonly performed weight loss surgery.

Vertical sleeve gastrectomy is typically performed using standard laparoscopic equipment. The greater curvature of the stomach is mobilized using vessel-sealing devices, sealing the gastric branches of the gastroepiploic vessels and the short gastric vessels. The posterior adhesions of the stomach are also divided so the stomach is fully mobilized while the blood supply to the lesser curvature remains intact.

Following mobilization of the stomach a calibration tube is typically introduced into the stomach through the mouth. Resection is accomplished by applying a series of staples from a laparoscopic linear surgical stapler, for example, along the calibration tube in a staple line. The staple line may be important in sleeve gastrectomy as the amount of weight lost and complications or consequences may be a direct result of the quality of the resultant sleeve gastrectomy pouch formed from the staple line (e.g., the portion of the stomach not rescinded by the staple line). The complications or consequences may include gastroesophageal reflux disorder (GERD), weight loss failure or weight regain, food intolerance, staple line bleed, leak, and/or the like.

To help produce a repeatable sleeve gastrectomy pouch (e.g., from the staple line), a sleeve gastrecotomy stapling guide and calibration tube with a constant diameter may be used. Although the combination of the stapling guide and calibration tube may help produce a better staple line and, thus, sleeve gastrectomy pouch, a surgeon may still need to estimate or envision an adequate distance from one or more parts of the stomach such as the IA to not create a stricture at that point with the staple line. Other efforts, devices, and techniques such as balloon catheters, bougies, and/or the like have been made to improve the calibration and, thus, location of the staple line such thereby needing less estimation by the surgeon. Unfortunately, such efforts still make it difficult for a surgeon to envision the staple line and may not help ensure that proper distances are maintained from each landmark along the stomach as the surgeon may still need to estimate distances to create the staple line.

SUMMARY

In an example herein, one or more medical devices may be provided that may be used, for example, in bariatric surgery including a vertical sleeve gastrectomy. The one or more medical devices may include a laparoscopic sleeve gastrectomy stapling guide in conjunction with a calibration tube in accordance with one or more examples. According to an example, the calibration tube may be a flared, multi-diameter calibration tube. The flared, multi-diameter calibration tube may have a first diameter along a portion of the tube and a second diameter that may larger than the first diameter along at least another portion of the tube. The calibration tube may be used in conjunction with the stapling guide to align stomach such that it may be stapled along the stapling guide (e.g., to perform the vertical sleeve gastrectomy). In examples herein, the one or more devices (e.g., the calibration tube and/or the stapling guide) may provide a proper distance (e.g., a minimum safe distance) from the incisura angularis and other stomach landmarks during the creation of a staple line for the vertical sleeve gastrectomy and may be used to create a repeatable resultant sleeve size of the stomach. For example, a surgeon may have a good idea of what size the resultant sleeve size should be, but the shortcoming of current methods, medical devices, and/or the like may lie in how they may be used to create and repeat such a sleeve—both between different surgeons, and for each surgeon from patient to patient. The use of the flared, calibration tube (e.g., with the different diameters) along with the staple guide may enable a surgeon to create the resultant sleeve size they desire, and a size they know works for effective weight loss while at the same time may improve a surgeon's ability to line up each staple fire and create the resultant sleeve that may be more consistent and repeatable.

BRIEF DESCRIPTION OF THE DRAWINGS

FIG. 13A is the formula used to calculate resultant sleeve circumference based on stapling guide width and calibration tube circumference.

FIG. 13B is the formula used to calculate resultant sleeve diameter based on stapling guide width and calibration tube diameter.

FIG. 14A depicts a cross-section view of what the calibration tube and stapling guide combination will look like, with the adjacent resection line along the guide.

FIG. 14B then depicts the resultant size of the sleeve once the calibration tube and stapling guide have been removed.

FIGS. 19-23 illustrate an additional or alternative example method or procedure that may be performed using the flared, calibration tube in one or more examples.

FIG. 33 depicts a table illustrating different sizes of the flared, calibration tube and/or the stapling guide that may provide different sizes to a resultant sleeve of a stomach in one or more examples herein.

DETAILED DESCRIPTION

Figure 1:
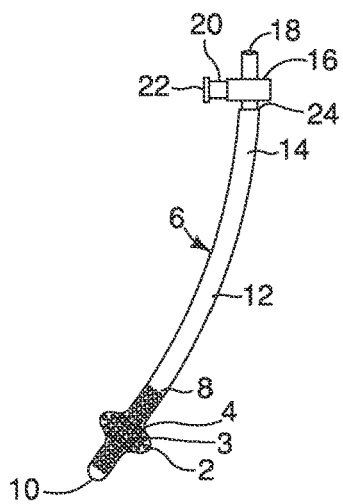
FIG. 1 depicts the flared calibration tube complete with a valve for regulated suction and perforations to allow for suction and injection of material into the stomach.

As described herein, systems and/or methods may be provided for performing a sleeve gastrectomy. For example, a first medical device may be positioned in an interior of the stomach. The first medical device may include or have a first diameter along a first portion thereof (e.g., a calibration or medical tube) and a second diameter that may be larger than the first diameter along a second portion thereof (e.g., a flared portion or a radially-outward projecting portion of a medical tube). The first medical device may be positioned, for example, by inserting the first medical device into a mouth of a patient to access the interior of the stomach and positioning the second portion at a landmark (e.g., a first landmark such as an incisura angularis (IA)) of the stomach. According to an example, the first medical device may be moved proximally and/or distally (e.g., from a first position to a second position) to position the first medical device at the landmark.

Further, in one example, a second medical device such as a clamp or stapler may be positioned on an exterior of the stomach relative to or based on an interaction with the first medical device (e.g., adjacent to, near, in proximity to, and/or interaction with the second portion of the first medical device) such that the second medical device may be configured to demonstrate or create a path such as a resection line or staple line) along the stomach at which the sleeve gastrectomy may be performed. As such, the first medical device may be used as a reference to position the second medical device. For example, an interaction (e.g., positioning the second medical device relative to the first medical device may position the second medical device in a desired position to demonstrate or provide the path. In one example, movement of the first medical device causes a corresponding movement or sliding of the second medical device (e.g., from a first position to a second position) along the exterior of the stomach to position the second medical device in the desired position to demonstrate the path. The second medical device may be fixed relative to another landmark and/or additional landmarks of the stomach (e.g., a second and/or a third landmark) as part of its positioning to create and/or demonstrate the path.

In additional examples, the first medical device itself may create and/or demonstrate the path to perform the sleeve gastrectomy as described herein (e.g., without use of the second medical device). In such an example the path may be demonstrated and/or created along the second portion (e.g., the flared portion) of the first medical device (e.g., the tube).

The sleeve gastrectomy (e.g., resection of part of the stomach) may be performed along the path thereby producing a resultant sleeve of the stomach. For example, a resection or staple line may be created (e.g., using a surgical stapler) along the path thereby producing the resultant sleeve. In one or more examples herein, the resultant sleeve of the stomach that may be created by the path (e.g., the resection or staple line) may include a diameter of approximately to 3 cm near the first landmark (e.g., the IA), approximately 2 to 6 cm near a second landmark (e.g., a pylorus) of the stomach, and approximately 0 to 2 cm near a third landmark (e.g., a gastroesophageal junction (GEJ) or GE junction) of the stomach.

In one example, the first medical device may be a flared, multi-diameter calibration tube and may include a tube that may include a flared portion at a distal end thereof. In an example, the tube may be the first portion and the flared portion may be the second portion. The tube may have or include a first diameter (e.g., a constant diameter as described herein) that may be proximal and distal to the flared portion. The flared portion may have or include a second diameter (e.g., a maximum diameter as described herein) that may be larger than the first diameter. As described herein, the tube (e.g., that may be the first medical device or part of the first medical device) may be configured to be inserted or may be inserted into an interior of the stomach and the flared portion may be positioned at a first landmark thereof (e.g., the IA) such that the flared portion that may be positioned at the first landmark may be configured to facilitate alignment of a resection line or staple line (e.g., the path) during the sleeve gastrectomy that produces the resultant sleeve described herein. For example, the flared portion may include a first point and a second portion at an opposite end thereof forming the second diameter thereacross. The first point of the flared portion may be configured to be positioned near the first landmark as described herein and the second point of the flared portion may be configured to form the resection line (e.g., a line that includes the second point) that produces the resultant sleeve.

In an example, alignment of resection or staple line may further be facilitated by the second medical device (e.g., a clamp or stapler) positioned relative to the first medical device. For example, the flared portion may include a first point and a second point at an opposite end thereof forming the second diameter thereacross. The first point of the flared portion may be configured to be positioned near the first landmark as described herein and the second medial device may be configured to be positioned near the second point of the flared portion to form the resection line (e.g., a line along a side of the clamp opposite of the side positioned near the second point) that produces the resultant sleeve.

FIG. 1 depicts the flared calibration tube complete with a valve for regulated suction and perforations to allow for suction and injection of material into the stomach. As shown in FIG. 1, a flared, calibration tube 12 (e.g., a first medical device) in accordance with one or more examples herein may be provided. According to an example herein, the flared, calibration tube 12 may be used in conjunction with a second medical device (e.g., a clamp or a surgical stapler) as described herein (not shown in FIG. 1 but an example of which may be shown as stapling guide 88 in FIGS. 15-32) to perform a vertical sleeve gastrectomy. In an example, the flared, calibration tube 12 may have a first diameter along a portion thereof that may be constant (e.g., 6) and a second diameter along another portion thereof (e.g., 2) that may be larger than the first diameter as described herein.

For example, as shown, the flared, calibration tube 12 may include a tube 14 (e.g., a first portion of the first medical device or calibration tube) and a suction regulation valve 16 that may cap the tube 14 (e.g., a body of the tube 14). As shown, the tube 14 may be generally cylindrical in shape and may be made of, for example, rubber, silicone, polyurethane, a plastic polymer, and/or any other suitable material. The tube may be hollow, solid, and/or the like in one or more examples. The tube 14 may include a proximal end PE that may be closer to a surgeon that may interact with the flared, calibration tube 12 to a distal end DE that may be farther away from the surgeon. As shown, the tube 14 may include a lower tip 10 at the distal end DE and a flared out portion 3 (e.g., a second portion of the first medical device or calibration tube) and may be capped off by the suction regulation valve 16 at the proximal end PE.

The lower tip 10 of the tube 14 may be long enough to allow for easy insertion into the mouth, esophagus, and stomach, and/or may enable or allow the tube 14 of the flared, calibration tube 12 to be navigated down to the pylorus of the stomach. Moving proximally up from the lower tip 10 at the distal end DE, the tube 14 (e.g., the generally cylindrical shape of the tube 14) may include a flared portion 3 (e.g., a cylindrical flared portion).

Figure 2:
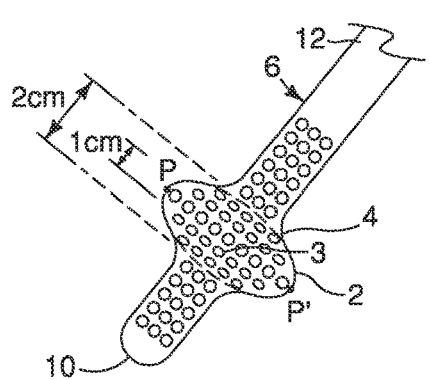
FIG. 2 depicts a zoomed-in look at the tip of the flared calibration tube, indicating the cylindrical flared portion along with the perforations.

FIG. 2 depicts an enlarged view of the lower tip 10 of the tube 14 that may be included in the flared, calibration tube 12 including the flared portion 3. As shown in FIG. 2, the tube 14 may begin to flare out 4 from the constant diameter 6 until it reaches the maximum diameter 2 at which point it may begin to flare in 5 until it may return back to the constant diameter 6 thereby forming the flared out portion 3. As described herein, the flared out portion 3 may be used to align and calibrate a stapling guide such that a more accurate staple line (e.g., path or resection line) may be formed for resection during the vertical sleeve gastrectomy according to examples herein. As shown, the maximum diameter 2 may be formed by points (e.g., a first and second point such as P and P') at opposite ends or sides of the flared portion 3.

In an example, the flared portion 3 may be approximately 2 cm long from the beginning of the flare 4 to the end of the flare 5. Further, as shown, the maximum diameter 2 of the flared portion 3 may be approximately. Additionally, as described herein (e.g., above), the flared portion 3 may narrow at 4 and 5 until it may return to the constant diameter 6 (e.g., that may be substantially maintained throughout the rest of the tube 14). Example dimensional ranges of the constant diameter portion 6 of the tube may be from 0.3 cm to 1.5 cm and example dimensional ranges of the flared portion 3 are contemplated to range from 0.5 cm to 2.0 cm (e.g., including the maximum diameter 2). Such ranges may be provided based on a spacer (e.g., the spacer 60) that may be 1 cm in width according the formulas F1 and F2 described with respect to FIGS. 13A-13B and 14A-14B. In one or more examples, the resultant sleeve diameter range may be 1 cm (or 30 French) to 2 cm (or 60 French) for the cylindrical portion near or above the incisura angularis (e.g., a first landmark), may be 2 cm to 6 cm for the portion near the pylorus (e.g., a second landmark), and/or 0 cm to 2 cm for the portion near the GEJ (e.g., a third landmark). The flared portion 3 may have a wider resultant sleeve diameter of 1.2 cm (or 36 French) to 2.6 cm (or 78 French) according to examples herein.

Figure 10:
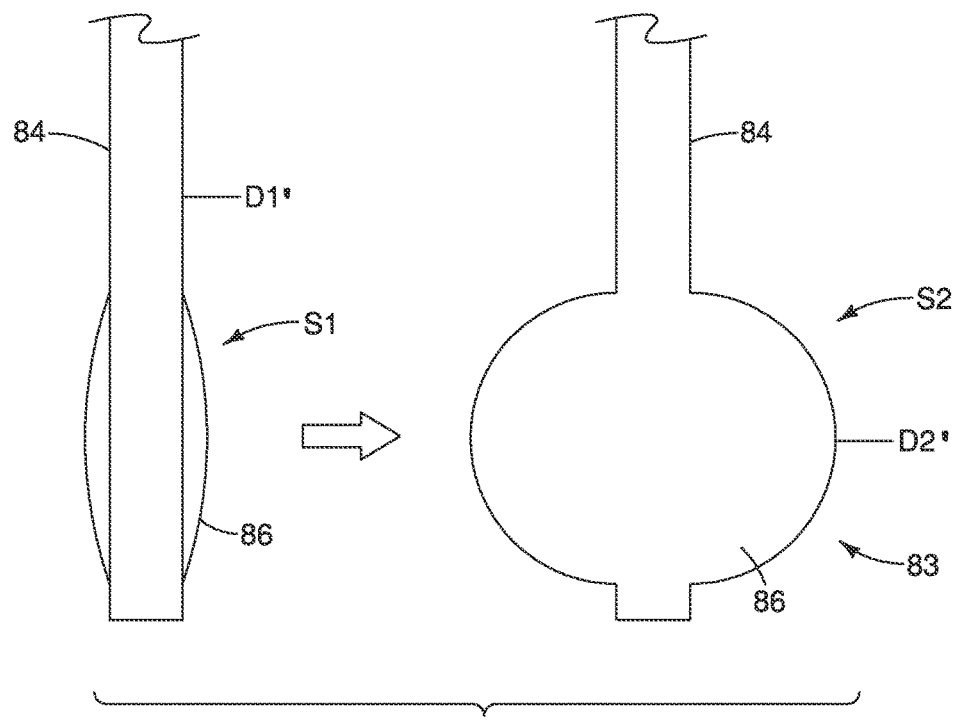
FIGS. 10-12B depicts an enlarged view of one or more additional or alternative examples of a flared portion that may be included in the flared, calibration tube.
Figure 11:
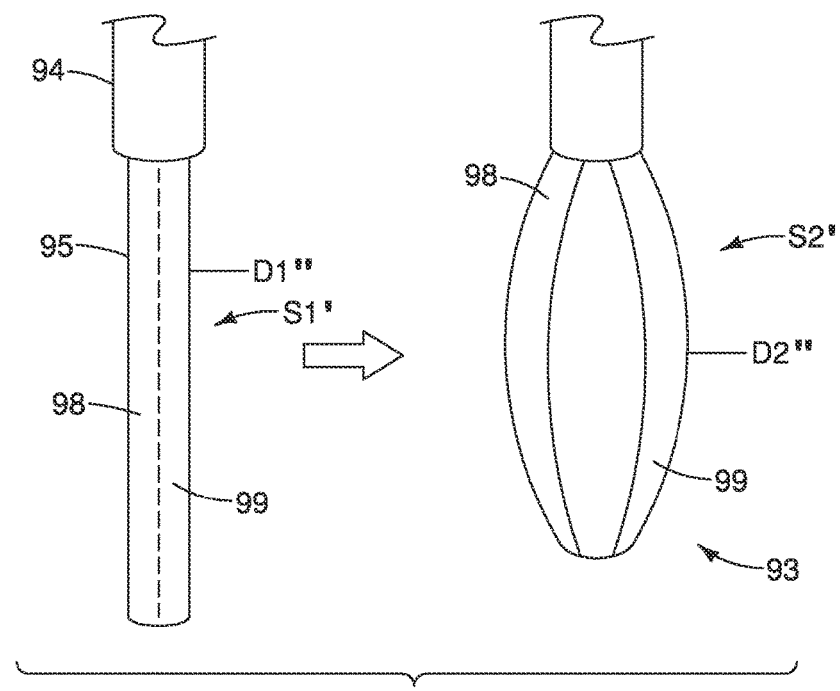

As shown in FIG. 2, according to one example, the flared portion 3 may be integrally formed as part of the tube 14, for example, during manufacturing. In additional or alternative examples, the flared portion 3 may be separately coupled and/or fixedly attached to the tube 14 and/or may include two separate pieces (e.g., as shown in FIGS. 4-8). In additional embodiments, the flared portion 3 may be a constant diameter (e.g., the constant diameter 6) and/or a smaller diameter than the constant diameter 6 until use of the flared, calibration tube 12 during the vertical sleeve gastrectomy during which the flared portion 3 may be enlarged to the maximum diameter 2 by inflation and/or actuation such as mechanical actuation (e.g., as shown in FIGS. 10-12).

In examples herein, the diameter 2 of the flared out portion 3 may be used as a form of alignment and calibration, and/or may be the point at which a stapling guide (not shown in FIG. 1 and which may be shown as 88 in FIGS. 15-32) may be positioned adjacent to an incisura angularis (IA) (e.g., not shown in FIG. 1 and which may be shown as 40d in FIGS. 15-32). As such, the flared, calibration tube 12

(e.g., via tube 14) may include a constant diameter 6 and a maximum diameter 2 (e.g., $D_1$ in FIG. 13A) of a flared portion 3 such that the flared, calibration tube 12 may enable a surgeon to more reliably create a sleeve pouch with a different (wider) diameter at the IA (e.g., $D_2$ in FIG. 13B) than the GE junction. In such an example, the stapling guide may be used as a spacer, otherwise, the flared portion 3 may not fit past the narrower upper sleeve of the stomach (e.g., 40e as shown in FIGS. 15-18).

In an example, as shown in FIG. 2, the tube 14 may include one or more perforations 26. For example, as shown, the lower tip 10, the flared portion 3, and/or a portion of the tube 14 proximal to the flared portion include the one or more perforations 26 therein. In an example, the one or more perforations 26 may be holes in the tube 14 that may be used to collect or suction tissue debris from the stomach that may be suctioned proximally up through the tube 14 during the vertical sleeve gastrectomy and expunged therefrom as described herein.

Referring back to FIG. 1, the body of the tube 14 may be capped 24 by a suction control valve 16 that may be used to regulate when and how suction may be applied to the distal end DE (e.g., shown in FIG. 2) of the tube 14. As shown, the suction control valve 16 may include a switch 22 that may be used to open and/or close the suction control valve thereby allowing and/or not allow air flow through the tube.

Figure 3A:
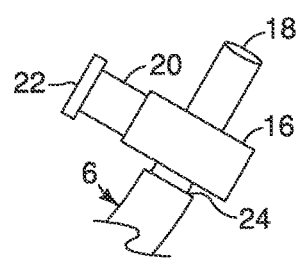
FIG. 3A depicts the suction regulation valve of the flared calibration tube in the "open" position.

FIG. 3A depicts the suction control valve 16 of the flared, calibration tube 12 in an "open" position 20. In an example, when the switch 22 of the valve 16 may be in the "open" position 20, air may flow out of the tube 14 through an opening at a proximal tip 18 of the flared, calibration tube 12. As described herein, in the "open" position 20, the suction control valve 16 may enable tissue debris to be removed during the vertical sleeve gastrectomy and expunged therefrom as described herein. For example, the debris that may be collected by the one or more perforations 26 may be suctioned through the tube 14 and out of the opening in the proximal tip 18 when the suction control valve 16 may be in the "open" position 20.

Figure 3B:
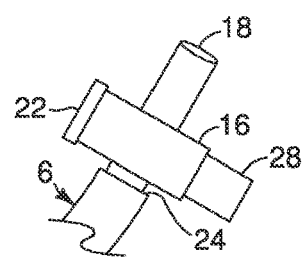
FIG. 3B depicts the suction regulation valve of the flared calibration tube in the "closed" position.

FIG. 3B depicts the suction control valve 16 of the flared, calibration tube 12 in a "closed" position 28. According to an example, when the switch 22 of the valve 16 may be in the "closed" position 28, air may not flow out (e.g., air may be blocked) of the tube 14 through the opening at a proximal tip 18 of the flared, calibration tube 12. In the "closed" position 28, tissue debris may not be expunged and/or removed during the vertical sleeve gastrectomy.

Figure 4:
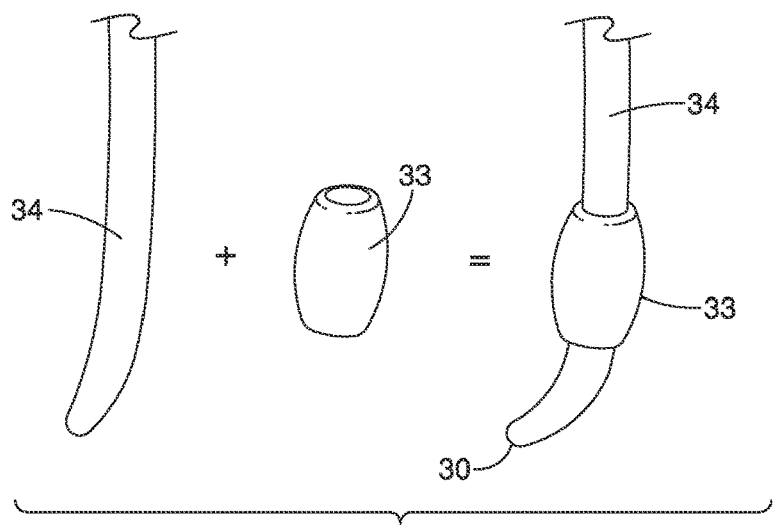
FIGS. 4-9 depicts an enlarged view of one or more additional or alternative examples of a flared portion that may be included in the flared, calibration tube.
Figure 5A:
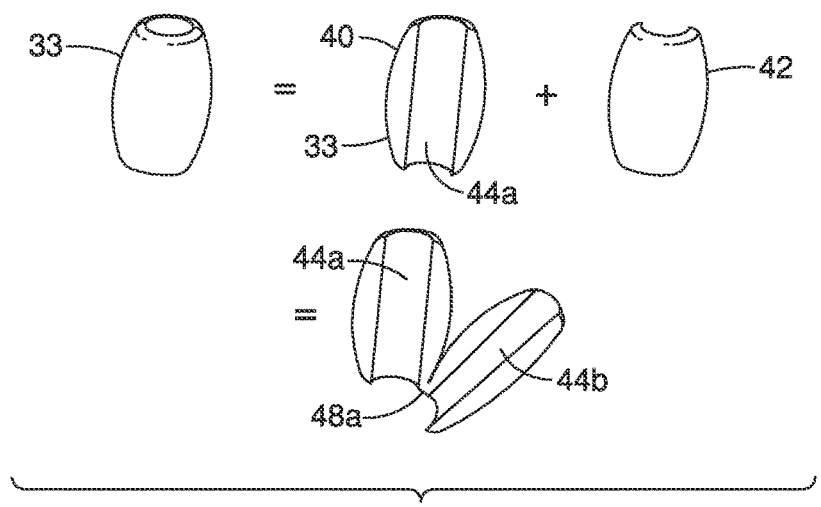
Figure 5B:
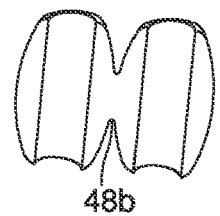
Figure 6:
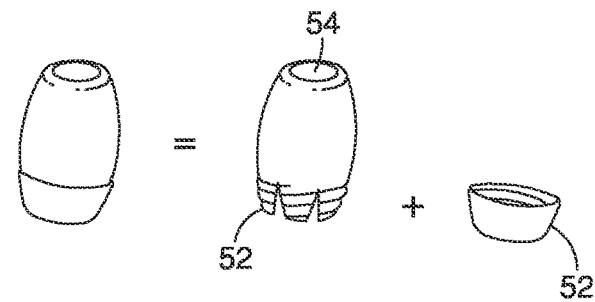
Figure 6:
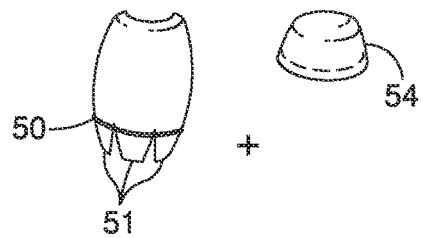

FIGS. 4-8 depicts an enlarged view of one or more additional or alternative examples of the flared portion 33 that may be included in the flared, calibration tube 12. As shown in FIGS. 4-6, a separate, flared portion 33 (e.g., that may have the same or similar properties including the maximum diameter 2, and/or the like as described herein with respect to the flared portion 3) may be coupled or attached onto an existing stock gastric tube 34 (e.g., that may have the same or similar properties including the constant diameter 6, and/or the like as described herein with respect to the tube 14). This may enable the flared portion 33 (e.g., the add on) to be sold separately and assembled at bedside or prior to the surgery. In examples herein, the flared portion 33 may be slid onto the tube 34, may be snapped around the tube 34, may be glued on the tube 34, and/or may be coupled and/or fixedly attached to the tube 34 using any other suitable coupling or attachment mechanism. The flared portion 33 may include and/or have a tapered face (e.g., similar to the flared portion 3 tapering to 4 and 5) to slide along the oropharyngeal, esophageal and gastric mucosa without damaging the mucosal surfaces and/or getting snagged. The flared portion 13 may be made rubber, silicone, polyurethane, a plastic polymer, and/or any other suitable material.

FIGS. 5A-5B illustrate examples of the flared portion 33 that may be coupled or attached onto the tube 34. As shown in FIG. 5A, the flared portion 33 may include a first flared portion 40 and a second flared portion 42. As shown, the first flared portion 40 and the second flared portion 42 may have crevices 44a, 44b respectively. The crevices 44a, 44b may be convex depression that may extend along the outer diameter of the tube 34 and may when combined take the shape of the outer diameter of the tube 34. For example, when the first and second portions 40, 42 may coupled or attached together (e.g., connected via one or more snaps (not shown), glue, and/or the like), the crevices 44a, 44b may receive and surround the tube 34. As shown in FIG. 5B, the first and second portions 40, 42 may include a hinge 48a, 48b that may be used to pivot the first and second portions, 40, 42 to surround the tube 34.

In an example, as shown in FIG. 6, the flared portion 33 may be used with different diameter tubes. For example, the flared portion 33 may include and/or have a gripping surface 50 and a screw 52 and/or cap 54 that may be inserted into one or more sides of the tube 34. The gripping surface 50 may include teeth 51 that may be used to prevent the flared portion 33 from sliding up and down the tube 34. For example, the flared portion 33 may be slid over the tube 34 and the teeth 51 of the gripping surface 50 may help secure the flared portion 33 at the appropriate location on the tube 34 thereby preventing the flared portion 33 from sliding freely up and down the tube 34. In one example (e.g., once the flared portion 33 may be positioned at the appropriate location), the screw may be inserted over the tube 34 and screwed, for example, in a distal end of the flared portion 33 and the cap 52 may be inserted over the tube 34 and snapped into a proximal end of the flared portion 33 thereby further securing the flared portion 33 on the tube 34 and preventing movement thereof.

Figure 7:
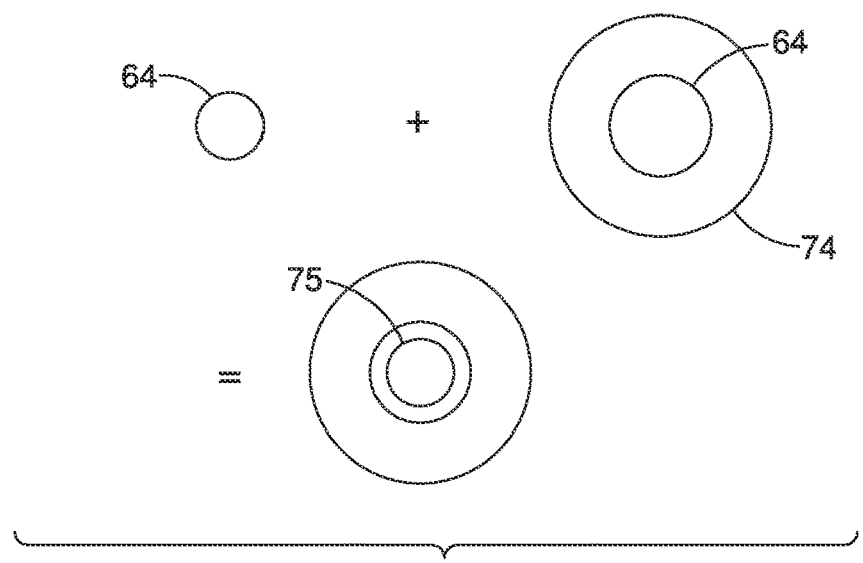
Figure 8:
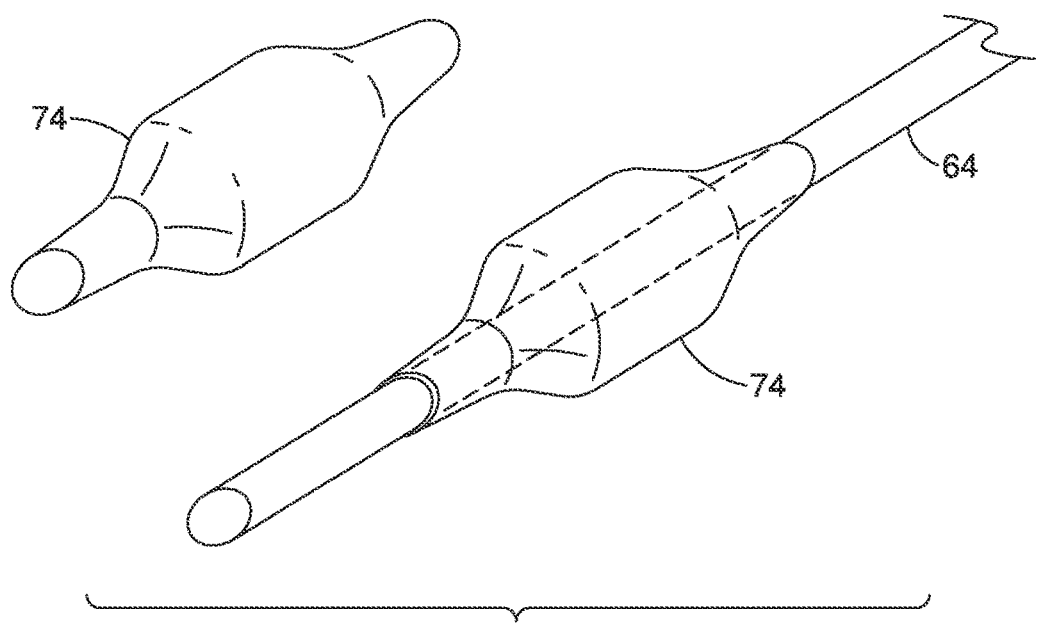

According to examples, as shown in FIGS. 7-8, a tube with two diameters (e.g., a first and second diameter) and/or a first and second tube 64, 74 may be inserted within each other may be used to form a flared portion 73 (e.g., that may have the same or similar properties including the maximum diameter 2, and/or the like as described herein with respect to the flared portion 3). For example, the first tube 64 may include a 16 or 18 French polymer or latex orogastric tube that may be used as the smaller diameter tube (e.g., that may have the same or similar properties of the tube 14 including the constant diameter 6, and/or the like). The second tube 74 may include a tapered wider section of a tube (e.g., a polymer or latex orogastric tube) with an inner diameter that may be equivalent to, larger, and/or substantially similar to the outer diameter of the tube 14 (e.g., constant diameter 6) and an outer diameter equivalent to the diameter of the flared portion 3 (e.g., the maximum diameter 2). Further, as shown in FIG. 8, the tube 74 may taper similar to the tapering 4,5 of the flared portion 3. According to an example, the second tube 74 may be slid over and positioned at the appropriate location on the first tube 64 (e.g., a location approximately near the distal end 10 similar to the flared portion 3). The second tube 74 (e.g., once positioned) may be fixedly attached and/or coupled to the first tube 64 via any suitable technique including solvent bonding via a solvent bond 75.

Figure 9:
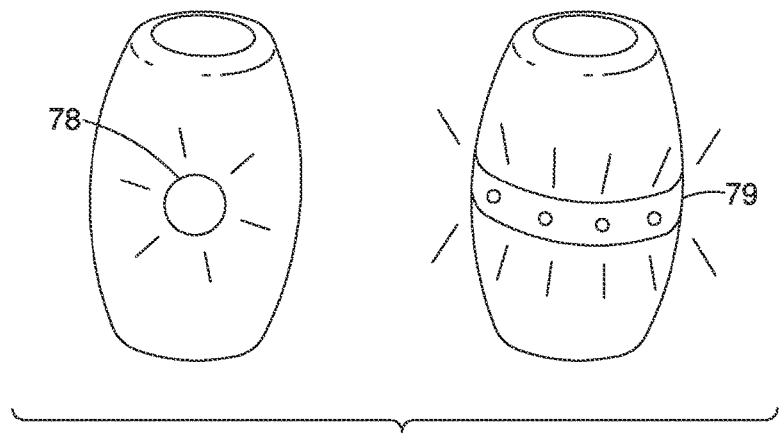

FIG. 9 illustrates an example of one or more lights that may be included in the flared portion 3, 33, and/or 73 in one or more examples. For example, the flared portion 3, 33, and/or 73 (e.g., the wider section) of the tubes 14, 34, and/or 74 (e.g., that may be combined with the tube 64) may be fitted with lights 78, 79 such as LED or fiber optic lights to better visualize the position of the tube within the stomach. According to an example, having lights 78, 79 that may indicate the flared portion may enable or the surgeon to accurately place the wider portion of the calibration tube adjacent the incisura angularis (IA).

FIGS. 10-12B depicts an enlarged view of one or more additional or alternative examples of the flared portion 83 that may be included in the flared, calibration tube 12. As shown in FIG. 10, in one example, a tube 84 that may be included in the flared, calibration tube 12 may include a first diameter D1' that may be adjustable to a second diameter D2' to form the flared portion 83. For example, the tube 84 may include a balloon 86 that may be used to form the flared portion 93. The balloon 86 may be relaxed or deflated prior to use and insertion of the flared, calibration tube 12 in the stomach. In such an example (e.g., prior to insertion and use), the tube 84 with the balloon 86 in the relaxed or deflated state S1 may have a substantially constant diameter (e.g., similar to the constant diameter 6). The first diameter D1' may be the substantially constant diameter. The balloon 86 may be inflated to an inflated state S2 upon insertion of the tube 84 that may be part of the flared, calibration tube 12 into the stomach to the appropriate position such as adjacent to the incisura angularis and interaction therewith. According to an example, the inflated state S2 may form the flared portion 83 that may have the second diameter D2' (e.g., similar to the maximum diameter 2). The tube 84 with the flared portion 83 formed by the balloon 86 may enable the staple line to be performed with a single cartridge sleeve gastrectomy stapler. For example, the tube 84 may be placed with the balloon 86 adjacent the incisura angularis (e.g., as described in FIGS. 24-28 below) in the state S1. The stapler may then placed in apposition but not fully clamped, the balloon may be inflated to the state S2 to form the flared portion 83, and the flared portion 83 formed by the balloon 86 in the state S2 may widen the area adjacent the incisura angularis prior to stapling. After stapling, the balloon 86 may be deflated to state S1 such that the tube 84 may return to the first diameter D1' and may be removed.

Further, as shown in FIG. 11, a tube 94 that may be included in the flared, calibration tube 12 may include a first diameter D1" that may be adjustable to a second diameter D2" to form the flared portion 93. For example, the tube 94 may include a split tube 95 at a distal end (e.g., the distal tip 10) and a solid portion 96 (e.g., that may have properties similar to the tube 14 including the constant diameter 6) extending proximally from the split tube 95 and the distal end. The split tube 95 may be used to form a flared portion 93 (e.g., that may have similar properties to the flared portion 3) similar to the balloon 86 used in the tube 84 described with respect to FIG. 10. In an example, the split tube 95 may include a first portion 98 and a second portion 99 that may be widened to form the flared portion 93. For example, the split tube 95 may be relaxed or compressed prior to use and insertion of the flared, calibration tube 12 in the stomach. In such an example (e.g., prior to insertion and use), the first and second portions 98, 99 of the split tube 95 may be in contact with each other in a relaxed or compressed state S1' such that the split tube 95 may have a substantially constant diameter (e.g., that may be similar and/or smaller than the constant diameter 6) that may be diameter D1". The split tube 95 may be widened (e.g., the first and second portions 98, 99 may be separated) from the relaxed or compressed state S1' to an expanded state S2' that may form the flared portion 93 upon insertion of the tube 94 into the stomach to the appropriate position such as adjacent to the incisura angularis and interaction therewith (e.g., similar to that described in FIGS. 24-28). Such an interaction may include, for example, shortening a distance from the distal tip to the solid portion of the tube 94 by pulling on a control element (e.g., at the proximal end of the tube 94 not shown). As shown, in the second state S2', the first and second portions 98, 99 of the split tube 95 may be adjusted from the first diameter D1" to a second diameter D2" (e.g. may become wider along an x-axis) the first and second portions 98, 99 may be wider along the x axis. In additional or alternative examples, the split tube 95 may include three portions, four portions, and/or the like that may be expanded and/or become wider along the x and z axes to form the flared portion 93.

Figure 12A:
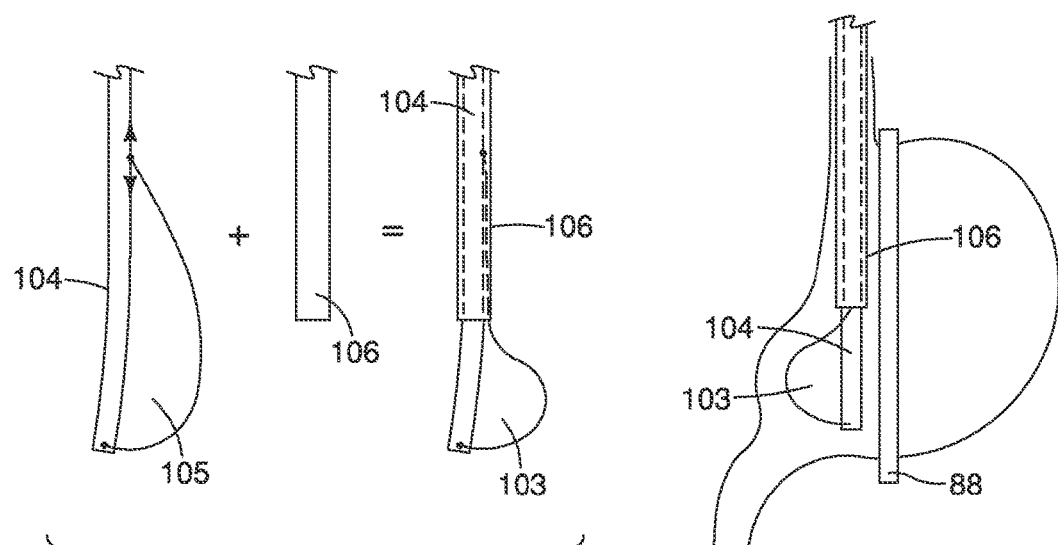
Figure 12B:
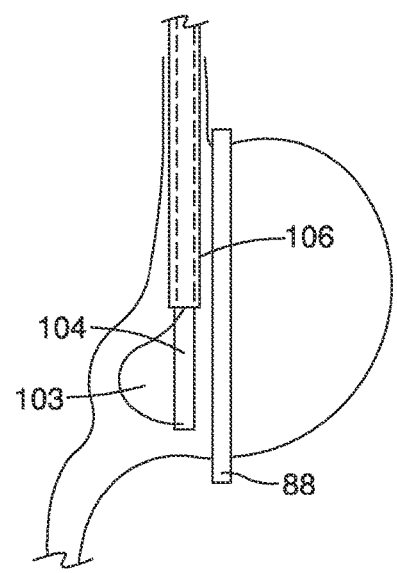

In an example as shown in FIG. 12A-12B, a tube 104 may include a bowing out portion that may be used to form the flared portion 103 that may be included in the flared, calibration tube 12. As described herein the tube 104 may include one or more properties similar to the tube 4 such as the constant diameter 6, and/or the like. Similarly, the flared portion 103 that may be formed may include one or more properties similar to the flared portion 3 such as the maximum diameter 2 (e.g., upon actuation and/or insertion). The flared portion 103 may be formed from bowing out a sail 105 attached to the tube 104 using a sheath 106. For example, the tube 104 may have a sail portion 105 (e.g., a portion that bows out) that may be connected to the tube 104 at the distal end and a second point 20 to 30 cm proximally. Alternatively, the sail portion 105 is connected distally and extends beyond the proximal end of tube 104. In this configuration, the sail portion 105 is extendable when portion extending beyond tube 104 is pushed into tube 104 and retractable when portion extending beyond tube 104 is lengthened. The sail portion 105 may be adjusted to form the fared portion 103, for example, by applying force thereto using a sheath 106, and/or the like. For example, the flared, calibration tube 12 may include a sheath 106. The sheath 106 may be inserted over the tube 104 at the proximal end (e.g., PE) to apply the force to the sail portion 105 thereby adjusting the sail portion 105 to form the flared portion 103 relative to tube 104. In an example, the tube 104 with the sail portion 105 may be inserted into the stomach and positioned such that the flared portion 103 when formed may be adjacent to the incisura angularis. The sheath 106 may then be pushed distally down the tube 104, and may be moved distally and/or proximally to form and adjust the area that bows out to form the flared portion 103. In an example, the sail portion 105 may be combined with either a stapler or a stapling guide to make the flared portion 103 and/or the resultant sleeve formed thereby wider at the incisura angularis.

FIGS. 13A-13B depict example formulas, F1 and F2, that may be used to calculate a resultant sleeve circumference and diameter, respectively, based on stapling guide width and calibration tube circumference, respectively.

As described herein, using the flared, calibration tube with a sleeve gastrectomy stapling guide may help to create a repeatable sleeve gastrectomy anatomy based on a size a surgeon may want to achieve for their patient. The formulas F1, $C_1 + 2L_1 = C_2$, and F2, $$D_1 + \frac{2L_1}{\pi} = D_2,$$

may be used such that the flared, calibration tube and the stapling guide or clamp may create a reproducible sleeve diameter. In examples, $D_1$ represents the diameter of the calibration tube used and $C_1$ represents its circumference (e.g., at the IA, or the narrowest point), $L_1$ represents the distance/width of the (e.g., top and bottom) stapling guide, $D_2$ represents the diameter of a resultant sleeve size, and/or $C_2$ represents its resultant circumference.

For example, a surgeon may aim or want to create a resultant sleeve size equivalent to using that of a 36 French (Fr) bougie (or 1.2 cm), which may be $D_2$. If the stapling guide may be 1 cm in width ($L_1$), using the formula F2, the diameter of the calibration tube may be approximately 0.5634 cm ($D_1$), or 16.9014 Fr. As such, to create a sleeve size resultant of using a 36 Fr bougie, a 16.9 Fr flared, calibration tube should be used in conjunction with a stapling guide.

As described herein, one of the main focuses of this process, and the calibration tube, is the fact that it keeps the resection line at least 2 cm off of the IA. The desired resultant diameter above was 36 Fr, but this is only equivalent to 1.2 cm. While 36 Fr is a good estimate of the average diameter of the various calibration tubes used, surgeons achieve the 2 cm IA offset by inserting their calibration tube, and stapling (i.e. estimating) slightly off the calibration tube, guessing at where they think 2 cm is.

To overcome this, the calibration tube may configured to flair out at its widest point (e.g., the maximum diameter 2 of the flared portion 3, 13, and/or 23), which may be the same point where it may be lined up adjacent to the IA and the stapling guide, and may create a resultant diameter of 2 cm. Inserting 2 cm as $D_2$ into F1, with $L_1$ still 1 cm, $D_1$ may be calculated as 1.3634 cm, or 40.9014 Fr. Thus, at its widest point, the flared, calibration tube may be about 41 Fr. The rest of the tube may narrow as it moves proximally (e.g., to 4) until it reaches the constant diameter or a smaller diameter such that this point in the tube, for example, the flared portion or maximum diameter thereof may be emphasized and easier to see from the surgeon's perspective. The 41 Fr flair may subsequently narrow to something closer to the examples described herein, of around 15 or 16 Fr, so the rest of the tube may not be as wide thereby facilitating fundus removal, which may be important to the procedure. This narrowing from the maximum diameter (e.g., to 4 and/or 5) may also allow the stapling guide to be positioned at the GEJ. Based on the width and shape of the stapling guide along with the diameter of the flared, calibration tube, a 1 cm offset from the GEJ and a squared off final cut may be provided (e.g., ensured). As such, in an example, with a 10 mm stapling guide as a spacer, a calibration tube with a 41 Fr flare portion and 16.9 Fr body, a surgeon may be able to achieve a safe distance from the incisura angularis and create a sleeve gastrectomy tube with a consistent resultant diameter of 36 Fr.

Further, in one or more examples, other surgeons may want 1.5 cm or 2.5 cm offset (e.g., even though a 2 cm offset at the IA may be believed to be ideal) or some other distance along their staple line, so various sizes of flared, calibration tubes may be used in one or more examples herein to accommodate surgeon needs to maximize what they think is the best, most effective sleeve. A table as shown in FIG. 33 with the different sizes $D_1$, $D_2$, $L_1$, $C_1$, and/or $C_2$ may be provided to assist a surgeon in knowing the resultant sleeve volume with different sizes of the flared, calibration tube and/or the stapling guide. As such, according to examples herein, different flared, calibration tubes with different diameters may be used with a stapling guide with a particular width to achieve a resultant sleeve diameter using the formulas F1 and F2 (e.g., calculated thereby).

FIG. 14A depicts a cross-section view of what the calibration tube and stapling guide combination will look like, with the adjacent resection line along the guide. In an example herein, the formula F1 illustrated in FIG. 13A may be used to calculate the resultant sleeve circumference 58 ($C_2$) from the circumference 54 of the calibration tube 50 used ($C_1$) and the width 60 ($L_1$) of a stapling guide 88 used as shown in FIG. 14A.

FIG. 14B depicts the resultant size of the sleeve once the calibration tube and stapling guide may be removed. In one or more examples herein, the formula F2 as described herein may be used. Here, the diameter 56 ($D_2$) of the resultant sleeve 40g may be calculated from the diameter 52 ($D_1$) of the calibration tube 50 used and the width 60 (L1) of the stapling guide 88 used.

Figure 15:
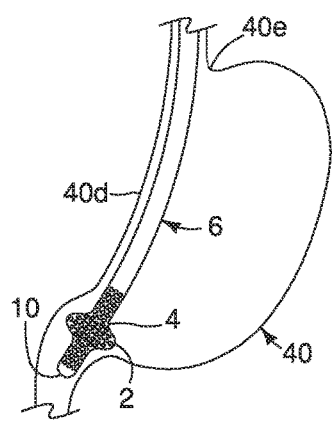
FIG. 15 depicts the flared calibration tube once it has been inserted to the pylorus of the stomach.
Figure 16:
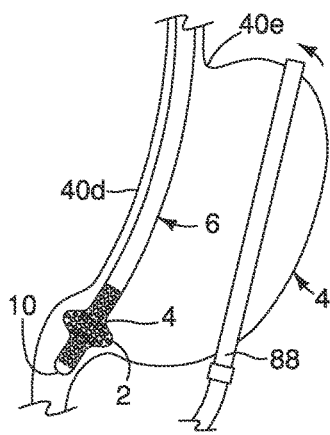
FIG. 16 depicts the stapling guide being positioned around the stomach.
Figure 17:
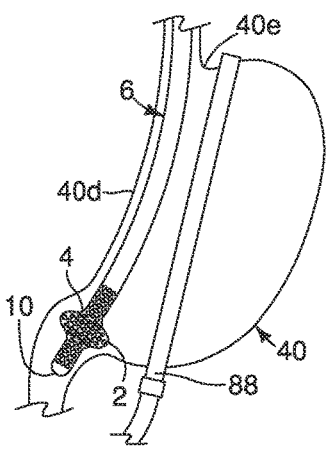
FIG. 17 depicts the stapling guide being positioned at the gastroesophageal junction, in the approximate location of where the resection line will occur.
Figure 18:
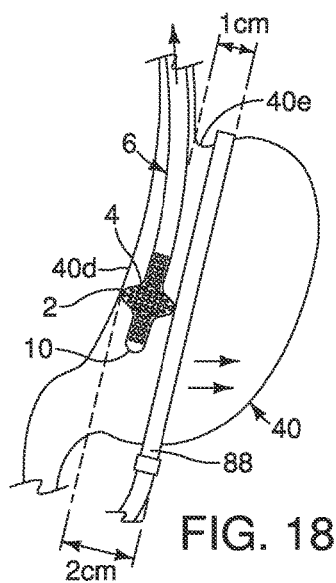
FIG. 18 depicts the calibration tube being pulled up from the pylorus and positioned along the incisura angularis, forcing the stapling guide to move laterally into the appropriate position to prepare for stapling and cutting.

FIG. 15-18 depicts an example method or procedure that may be performed using the flared, calibration tube 12 in one or more examples. As shown in FIG. 15, the calibration tube 12 may be positioned into an interior of a stomach. For example (e.g., to position), the calibration tube 12 may be inserted into a stomach 40 through the mouth and esophagus, and passed down into the pylorus. A stapling guide 88 may be positioned on an exterior of the stomach relative to the calibration tube 12. For example, the stapling guide 88 may be passed around the stomach 40 as shown in FIG. 15 until it may be placed into position, with the proximal portion being on the GE junction 40e as shown in FIG. 17. In examples, the stapling guide 88 may be inserted through a trocar or laparoscopic device to be positioned on the exterior of the stomach. The flared, calibration tube 12 may then be pulled up by the surgeon until the flared portion 3 (e.g., the maximum diameter 2 thereof) of the tube 14 may reach the incisura angularis 40d as shown in FIG. 18. Because the gap between the incisura angularis 40d and the stapling guide 88 may be narrower than the flared portion 3 of the tube 14, as the flared portion 3 moves vertically, it (e.g., via the point P') may push (e.g., a side of) the stapling guide 88 to the anatomic left that the stapling guide 88 may be positioned relative to. The surgeon may hold the stapling guide 88 in place at the GE junction 40e, so that the stapling guide 88 may swing over and create a line (e.g., along point P1, P2, and P3 as shown in FIGS. 18 and 19 and opposite to a side positioned relative to the calibration tube 12) up the stomach 40. In examples, P1 may be the distance from the pylorus, which may vary from surgeon to surgeon, but may typically be 2-6 cm from the pylorus on the gastric antrum along the greater curve (e.g., and may be 40c of the resultant sleeve in FIG. 30), P2 may be adjacent to the incisura angularis, and P3 may be the distance from the gastroesophageal junction (GEJ) (e.g., and may be 40e in FIGS. 15-18 and the resultant sleeve of FIG. 30). Further, P2 may be defined by an internal diameter of the flared portion 3 of the tube 14 plus the spacer effect of the stapling guide (e.g., using the formula F1 and F2 described with respect to FIGS. 13A-13B). The edge of the stapling guide 88 (e.g., where a surgical stapler may be deployed and the staple line formed along P1, P2, and P3) may then be approximately 2 cm off of the incisura angularis 40d and approximately 1.0 cm off of the GE junction 40e (e.g., which as described herein may be ideal for the surgeon).

In an example (e.g., when the stapling guide 88 may be so aligned), the stomach portions may be separated and reconnected along the edge of the stapling guide 88 at the path, staple line, resection line, or line (e.g., formed by P1, P2, and P3) using the surgical stapler such as a conventional surgical stapler. In the example described above, the stapling guide and the surgical stapler may be separate elements. In an additional or alternative embodiment, however, the stapling guide and the surgical stapler may be integrated into a single device. Once that device may be aligned, such as with the calibration tube described above, it may be activated as described herein to form the staple line along the vertical line thereby separating and reconnecting the stomach portions without further positioning.

Figure 30:
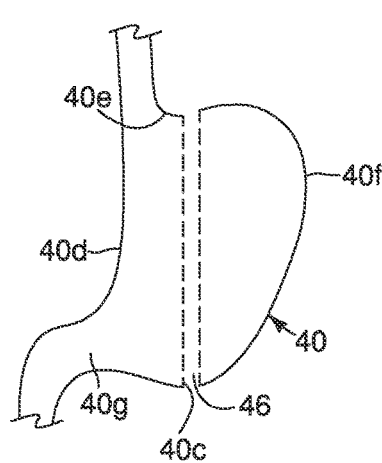
FIG. 30 depicts the resultant sleeve after the stapling and cutting has been executed. The resection line is about 2 cm off the incisura angularis, about 1 cm off of the GE junction, is vertical, and has complete fundus removal.

The resultant sleeve 40g, post stapling, may be illustrated in FIG. 30. The example dimensions (e.g., about 2 cm off of the incisura angularis 40d and about 1 cm off of the GE junction 40e) may be provided for the resultant sleeve 40g. For example, the resultant sleeve 40g created or provided by the path, resection line, staple line, or line may include a diameter of 1 to 3 cm near the first landmark (e.g., the IA 40d), 2 to 6 cm near a second landmark (e.g., a pylorus near 40c) of the stomach, and 0 to 2 cm near a third landmark (e.g., a gastroesophageal junction (GEJ) or GE junction 40e) of the stomach.

FIGS. 19-23 illustrate another or additional example method or procedure that may be performed using the flared, calibration tube 12 in one or more examples. As shown, in examples, the method or procedure shown in FIGS. 19-23 may be used with the tubes 64, 74 with the flared portion 73 described with respect to FIGS. 7-8 and/or the tube 34 with the flared portion 33 described with respect to FIGS. 4-6 (not shown). FIG. 19 shows the points P1, P2, and P3 on the stomach that a surgeon may want to form a staple line as described herein (e.g., in FIGS. 15-18) to create a sleeve gastrectomy associate with such points. As described herein, in one or more examples, different surgeons may have different methods and distances that they may be trying to achieve but they may want it wider at P2 to prevent kinking around the bend although the width may vary from 50% wider to 300% wider between the surgeons. Further, with respect to P3 (e.g., 40c in FIGS. 18 and 30), the surgeons may try to stay 0.5 cm to 1 cm away from the GEJ to preserve the sling fibers of the cardia, which play a role in the antireflux mechanism.

As shown in FIG. 20, an orogastric tube (e.g., as shown the first and second tubes 64, 74) with a flared portion (e.g., the flared portion 73) may be positioned in an interior of the stomach. For example (e.g., to position), the first and second tubes 64, 74 may be inserted into the stomach 40 through the mouth and esophagus, and passed down into the pylorus. The tubes 64, 74 may be placed along the lesser curve such that the flared portion 73 with the wider diameter (e.g., the maximum diameter 2) may be placed at the incisura angularis 40d. The stapling guide 88 may be positioned on an exterior of the stomach relative to the tubes 64, 74. For example, the stapling guide 88 may be passed around the stomach 40 as shown in FIG. 21 until it may be placed into position (e.g., near point P'), with the proximal portion being on the GE junction 40e as shown in FIG. 22. For example, as shown in FIG. 21, the stapling guide 88 may be placed just medial to the desired resection line, staple line, or line that may be defined by P1 to P2. In an example, P2 may be defined by an internal diameter of the flared portion 23 of the orogastric tube (e.g., 64 and 74) plus the spacer effect of the stapling guide (e.g., using the formula F1 and F2 described with respect to FIGS. 13A-13B). As shown in FIGS. 21 and 22, the surgeon may move the stapling guide 88 relative to the stomach 40 to align P2 with P3 such that P1, P2, and P3 may be in alignment and adjacent to a lateral edge or side of the surgical clamp 88 (e.g., opposite to an edge or side near or adjacent to the point P') ready to be stapled therealong to form or create the staple line, line, resection line, or path. As described herein, the edge of the stapling guide 88 (e.g., where a surgical stapler may be deployed and the staple line formed) may be approximately 2 cm off of the incisura angularis 40d and approximately 1.0 cm off of the GE junction 40e (e.g., which as described herein may be ideal for the surgeon) as shown in FIG. 22. The surgical stapler may be actuated along the line defined by P1, P2, and P3 as described herein.

The resultant sleeve 40g, post stapling along the line of P1, P2, and P3, may be illustrated in FIG. 23. The resultant sleeve 40g and its dimensions (e.g., about 2 cm off of the incisura angularis 40d and about 1 cm off of the GE junction 40e) may be provided. For example, the resultant sleeve 40g created or provided by the path, resection line, staple line, or line may include a diameter of 1 to 3 cm near the first landmark (e.g., the IA 40d), 2 to 6 cm near a second landmark (e.g., a pylorus near 40c) of the stomach, and 0 to 2 cm near a third landmark (e.g., a gastroesophageal junction (GEJ) or GE junction 40e) of the stomach. In an example, the lengths of the lines defined by P1 to P2 and P2 to P3 may be changed during clamping thereby enabling the formation of the resultant sleeve 40g and its dimensions. The orientation and position of the stomach may be changed in examples by the placement of the tubes 64, 74 and the stapling guide 88 and the stomach may snap back into shape after the manipulation and stapling. Thus, the interaction between the clamp 88 and the flared calibration tube 64, 74 aligns the points P1, P2 and P3 to enable a straight staple line to become a curved resultant sleeve.

Figure 24:
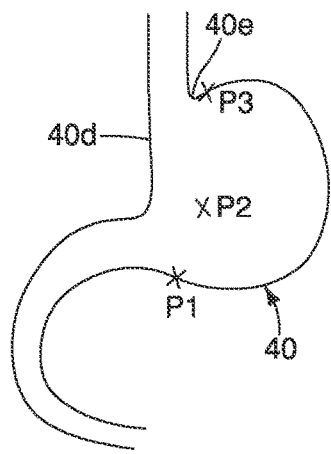
FIGS. 24-28 illustrate an additional or alternative example method or procedure that may be performed using the flared, calibration tube in one or more examples.

FIGS. 24-28 illustrate another or additional example method or procedure that may be performed using the flared, calibration tube 12 in one or more examples. As shown, in examples, the method or procedure shown in FIGS. 24-28 may be used with the tubes 84 with the flared portion 83 described with respect to FIG. 10 and/or the tubes 94, 104 with the flared portion 93,103 described with respect to FIGS. 11-12B (not shown). As shown in FIG. 24, similar to the method or procedure described above with respect to FIGS. 15-18 and 19-23, a surgeon may want to form a staple line or resection line along the line defined by P1, P2, and P3.

Figure 25:
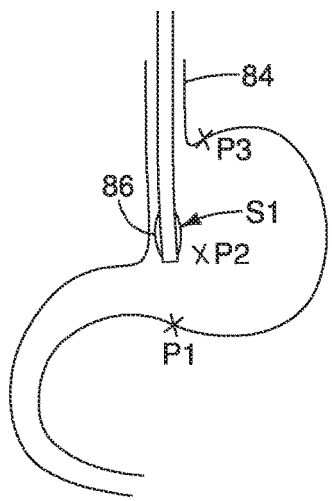

In FIG. 25, a calibration tube such as the tube 84 with a balloon such as the balloon 86 on the distal end (e.g., in state S1 as described above) that may form the flared portion 83 may be positioned in an interior of the stomach. For example, the tube 84 may be inserted into the stomach 40 through the mouth and esophagus, and passed down into the pylorus. The tube 84 may be inserted such that the balloon 86 that may form the flared portion 83 may be placed along the lesser curve adjacent the incisura angularis 40d.

Figure 26:
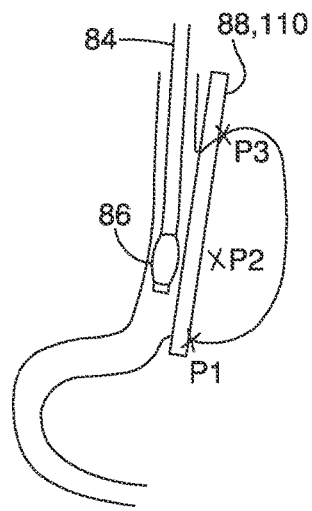

In an example, as shown in FIG. 26, a single cartridge stapler 110 or the stapling guide 88 may be positioned on an exterior of the stomach. For example, the stapler 110 may be placed along P1 and P3 or the stapling guide 88 may be placed medial to P1 and P3. P1 and P3 may be stabilized by partial clamping the stapler 110 or positing the stapling guide 88 as described herein (e.g., above), and/or using similar stabilization with accessory instruments.

Figure 27:
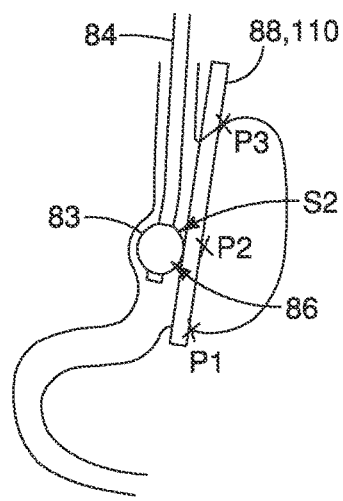

As shown in FIG. 27, the balloon 86 may be inflated (e.g., from state S1 to state S2 as described above) to form the flared portion 83. The flared portion 83 formed by the balloon 86 may align P2 with P1 and P3 as described herein by moving or the stapler 110 and/or the stapling guide 88 and/or the stomach to create or demonstrate the stapling line, resection line, path, and/or the like. For example, the flared portion 83 via the point P' that may be near an edge or side of the stapler 110 or stapling guide 88 may move the stapler 110 or stapling guide 88 to create the staple line, resection line, path, line, and/or the like (e.g., with the points P1, P2, and P3) along the edge of the stapler 110 or stapling guide 110 opposite of the edge near the point P'. As described herein, the edge of the stapler 110 or the stapling guide 88 (e.g., where a surgical stapler may be deployed and the staple line formed) may be approximately 2 cm off of the incisura angularis 40*d* and approximately 1.0 cm off of the GE junction 40*e* (e.g., which as described herein may be ideal for the surgeon) as shown in FIG. 22. The stapler may be actuated along the line defined by P1, P2, and P3 as described herein above. This may also be illustrated for the tube 104 in FIG. 12B.

Figure 28:
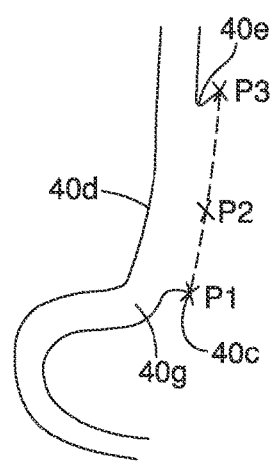

The resultant sleeve 40*g*, post stapling along the vertical line of P1, P2, and P3, may be illustrated in FIG. 28. The resultant sleeve 40*g* and its dimensions (about 2 cm off of the incisura angularis 40*d* and about 1 cm off of the GE junction 40*e*) may be provided. For example, the resultant sleeve 40*g* created or provided by the path, resection line, staple line, or line may include a diameter of 1 to 3 cm near the first landmark (e.g., the IA 40*d*), 2 to 6 cm near a second landmark (e.g., a pylorus near 40*c*) of the stomach, and 0 to 2 cm near a third landmark (e.g., a gastroesophageal junction (GEJ) or GE junction 40*e*) of the stomach. After the stapler may be removed, the stomach may return to a curved shape after resection as described herein.

Figure 29:
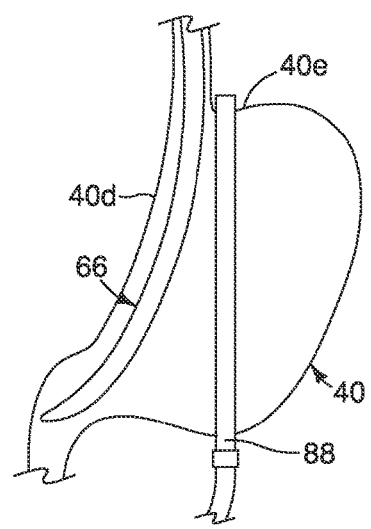
FIG. 29 depicts a calibration tube that is meant to generally represent the alternative embodiments listed above, used in conjunction with the stapling guide to assist in guide and resection line alignment.

FIG. 29 may illustrate a representation of what an example method or procedure may include if one of several alternative or additional examples may be used. Here, the example device 66 may be used similar to the flared calibration tube 12 in that it may help align the stapling guide 88 and create proper spacing as described herein to provide a resultant sleeve 40*g*.

Figure 31:
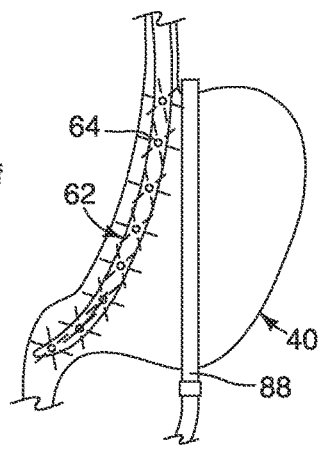
FIG. 31 depicts a calibration tube in accordance with another embodiment of the invention and used in conjunction with a stapling guide to assist in guide and resection line alignment.
Figure 32:
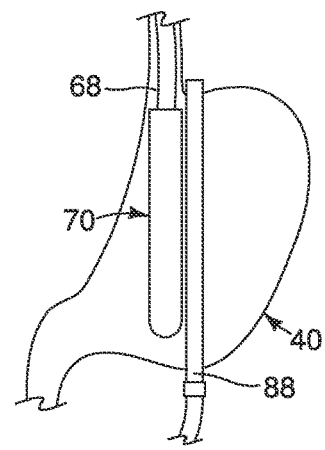
FIG. 32 depicts a calibration tube in accordance with another embodiment of the invention and used in conjunction with a stapling guide to assist in guide and resection line alignment.

Additional or alternative examples of the calibration tubes that may be used in FIG. 29 may be provided in FIGS. 31 and 32. FIG. 31 illustrates a calibration tube 62 with lights 64 running down the length of the tube 62. The lights 64 may assist the surgeon in seeing the placement and outline of the tube and improve their understanding of what their resultant sleeve will look like. The exact number and spacing of the lights 64 may vary to achieve the desired illumination. Further, FIG. 32 illustrates a specialized balloon bougie 68 that may be inflated to create a variable-sized balloon 70 that may be used to regulate the spacing to the stapling guide or single cartridge sleeve gastrectomy stapler and the volume of the sleeve. According to examples herein, the balloon 70 may be configured to have a consistent size and shape such that the sleeve may be sized and shaped to this template with the use of the stapling guide or single cartridge sleeve gastrectomy stapler. Thus, the balloon 70 may act as a mold from which to create the resultant sleeve lumen at a constant pressure (15 to 100 cm of water). Using either the tube 62 or the bougie 68, a resultant sleeve may be provided with the dimensions described herein as shown by 40*g* in FIG. 30 or similar dimensions to that of 40*g*.

While several devices and components thereof have been discussed in detail above, it should be understood that the components, features, configurations, and methods of using the devices discussed are not limited to the contexts provided above. In particular, components, features, configurations, and methods of use described in the context of one of the devices may be incorporated into any of the other devices. Furthermore, not limited to the further description provided below, additional and alternative suitable components, features, configurations, and methods of using the devices, as well as various ways in which the teachings herein may be combined and interchanged, will be apparent to those of ordinary skill in the art in view of the teachings herein.

Versions of the devices described above may be actuated mechanically or electromechanically (e.g., using one or more electrical motors, solenoids, etc.). However, other actuation modes may be suitable as well including but not limited to pneumatic and/or hydraulic actuation, etc. Various suitable ways in which such alternative forms of actuation may be provided in a device as described above will be apparent to those of ordinary skill in the art in view of the teachings herein.

Versions of the devices described above may have various types of construction. By way of example only, any of the devices described herein, or components thereof, may be constructed from a variety of metal and/or plastic materials.

Having shown and described various versions in the present disclosure, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

What is claimed is:

1. A method for performing a sleeve gastrectomy, the method comprising the steps of:
   providing a calibration tube having a tube portion and a flared portion at about a distal end of the tube portion, the tube portion having a first diameter and the flared portion having a second diameter larger than the first diameter;
   inserting the calibration tube into an interior of a stomach such that the flared portion is positioned at about an incisura angularis along a lesser curvature of the stomach;
   providing a single-use, single cartridge, linear sleeve gastrectomy stapler having a first end and a second end and having a length therebetween, the length extending from about a pylorus of the stomach to about a gastroesophageal junction (GEJ) of the stomach;
   positioning the first end of the single-use, single cartridge, linear sleeve gastrectomy stapler on an exterior of the stomach relative to and anatomically lateral to the flared portion of the calibration tube such that the first end of the single-use, single cartridge, linear sleeve gastrectomy stapler is positioned about one centimeter to about three centimeters laterally from the flared portion of the calibration tube;
   positioning the second end of the single-use, single cartridge, linear sleeve gastrectomy stapler about zero to about two centimeters relative to and anatomically lateral to the calibration tube at the GEJ;
   operating the single-use, single cartridge, linear sleeve gastrectomy stapler to provide a staple line; and
   cutting the stomach using the single-use, single cartridge, linear sleeve gastrectomy stapler to resect a portion of the stomach to form a sleeve.

2. The method of claim 1, wherein the flared portion of the calibration tube comprises a balloon that is inflated and deflated from at about a proximal end of the tube portion.

3. A method for performing a sleeve gastrectomy, the method comprising the steps of:

providing a calibration tube having a tube portion;

inserting the tube portion into an interior of a stomach, wherein the tube portion includes a flared portion positioned at about a distal end of the tube portion;

providing a single-use, single cartridge, linear sleeve gastrectomy stapler having a substantially linear length operably sized to extend from at about a pylorus of the stomach to at about a gastroesophageal junction (GEJ) of the stomach;

positioning, the single-use, single cartridge, linear sleeve gastrectomy stapler on an exterior of the stomach relative to and anatomically lateral to the calibration tube such that a substantially linear resection line for the sleeve gastrectomy is defined by the flared portion of the calibration tube and the single-use, single cartridge, linear sleeve gastrectomy stapler;

operating the single-use, single cartridge, linear sleeve gastrectomy stapler and the calibration tube thereby forming a single staple line and; and cutting the stomach using the single-use, single cartridge, linear sleeve gastrectomy stapler to resect a portion of the stomach to form a sleeve.

4. The method of claim 3, wherein the flared portion has a second diameter larger than a first diameter of the tube portion.

5. The method of claim 4, wherein the flared portion includes a balloon that is inflated and deflated from at about a proximal end of the tube portion.

6. The method of claim 2, wherein the balloon has a first deflated position for insertion into the stomach and a second inflated position for laterally displacing the lesser curvature of the stomach.

7. The method of claim 6, the balloon having a first diameter in the first deflated position and a second diameter in the second inflated position, wherein the second diameter is from about 0.5 cm to about 2 cm.

8. The method of claim 7, wherein the first diameter of the balloon in the first deflated position is substantially the same as the first diameter of the tube portion.

* * * * *